(12) United States Patent
Ly et al.

(10) Patent No.: US 8,563,544 B2
(45) Date of Patent: Oct. 22, 2013

(54) 2,5-DISUBSTITUTED ARYLSULFONAMIDE CCR3 ANTAGONISTS

(71) Applicant: Axikin Pharmaceuticals, Inc., San Diego, CA (US)

(72) Inventors: Tai Wei Ly, San Diego, CA (US); Garrett Thomas Potter, San Diego, CA (US)

(73) Assignee: Axikin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/662,080

(22) Filed: Oct. 26, 2012

(65) Prior Publication Data

US 2013/0065889 A1 Mar. 14, 2013

Related U.S. Application Data

(62) Division of application No. 12/764,249, filed on Apr. 21, 2010, now Pat. No. 8,318,747.

(60) Provisional application No. 61/171,626, filed on Apr. 22, 2009.

(51) Int. Cl.
| | |
|---|---|
| *C07D 211/96* | (2006.01) |
| *C07D 295/26* | (2006.01) |
| *C07D 241/08* | (2006.01) |
| *A61K 31/54* | (2006.01) |
| *A61K 31/4453* | (2006.01) |
| *A61K 31/445* | (2006.01) |

(52) U.S. Cl.
USPC ......... 514/227.5; 544/58.1; 544/58.2; 544/59

(58) Field of Classification Search
USPC ................ 544/58.1, 58.2, 59; 514/227.5
See application file for complete search history.

(56) References Cited

U.S. PATENT DOCUMENTS

| 7,071,180 B2 | 7/2006 | Nilsson et al. |
| 7,674,797 B2 | 3/2010 | Li et al. |
| 7,700,586 B2 | 4/2010 | Li et al. |
| 7,759,339 B2 | 7/2010 | Aertgeerts et al. |
| 2009/0286771 A1 | 11/2009 | Li et al. |

FOREIGN PATENT DOCUMENTS

| WO | WO 03/022277 | 3/2003 |
| WO | WO 2004/084898 | 10/2004 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Bischoff, et al., "Immunnohistological assessment of intestinal eosinophil activation in patients with eosinophilic gastroenteritis and inflammatory bowel disease," *Am. J. Gastroenterol.* 1999, 94, 3521-3529.
Combadiere, et al., "Cloning and functional expression of a human eosinophil CC chemokine receptor." *J. Biol. Chem.* 1995. 270, 16491-16494.
Durham, et al., "Eosinophils, bronchial hyperreactivity and late-phase asthmatic reactions," *Clin. Allergy* 1985, 15, 411-418.
Durham, "Mechanisms of mucosal inflammation in the nose and lungs," *Clin. Exp. Allergy* 1998, 28 Suppl. 2, 11-16.
Evans, et al., "Pretreatment with antibody to eosinophil major basic protein prevents hyperresponsiveness by protecting neuronal M2 muscarinic receptors in antigen-challenged guinea pigs," *J. Clin. Invest.* 1997, 100, 2254-2262.
Fulkerson, et al., "A central regulatory role for eosinophils and the eotaxin/CCR3 axis in chronic experimental allergic airway inflammation," *Proc. Natl. Acad. Sci. USA* 2006, 103, 16418-16423.
Grimaldi, et al., "Depletion of eosinophils in mice through the use of antibodies specific for C-C chemokine receptor 3 (CCR3)," *J. Leukocyte Biol.* 1999, 65, 846-853.
Heath, et al., "Chemokine receptor usage by human eosinophils. The importance of CCR3 demonstrated using an antagonistic monoclonal antibody," *J. Clin. Invest.* 1997, 99, 178-184.
Humbles, et al., "The murine CCR3 receptor regulates both the role of eosinophils and mast cells in allergen-induced airway inflammation and hyperresponsiveness," *Proc. Natl. Acad. Sci. USA* 2002, 99, 1479-1484.
Justice, et al., "Ablation of eosinophils leads to a reduction of allergen-induced pulmonary pathology," *Am. J. Physiol. Lung Cell. Mol. Physiol.* 2003, 284, L169-L178.

(Continued)

*Primary Examiner* — Kahsay Habte
(74) *Attorney, Agent, or Firm* — Jones Day

(57) ABSTRACT

Provided herein are 2,5-disubstituted arylsulfonamide CCR3 antagonists, e.g., compounds of Formula I, and pharmaceutical compositions thereof. Also provided herein are methods of their use for treating, preventing, or ameliorating one or more symptoms of a CCR3-mediated disorder, disease, or condition.

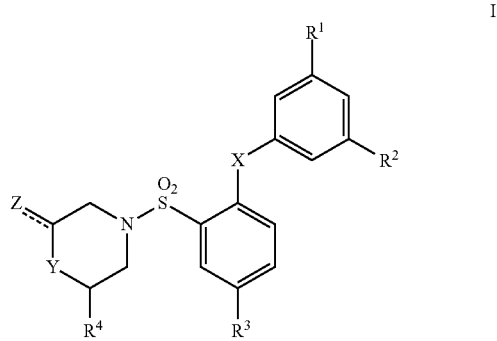

20 Claims, No Drawings

(56) References Cited

OTHER PUBLICATIONS

Kroegel, et al., "Blood and bronchoalveolar eosinophils in allergic subjects after segmental antigen challenge: surface phenotype, density heterogeneity, and prostanoid production," *J. Allergy Clin. Immunol.* 1994. 93, 725-734.

Leung, "Pathogenesis of atopic dermatitis," *J. Allergy Clin. Immunol.* 1999. 104, S99-108.

Ma, et al., "CCR3 is essential for skin eosinophilia and airway hyperresponsiveness in a murine model of allergic skin inflammation," *J. Clin. Invest.* 2002, 109, 621-628.

Pope, et al., "The eotaxin chemokines and CCR3 are fundamental regulators of allergen-induced pulmonary eosinophilia," *J. Immunol.* 2005, 175, 5341-5350.

Post, et al., "Molecular characterization of two murine eosinophil beta chemokine receptors," *J. Immunol.* 1995, 155, 5299-5305.

Ying, et al., "Eosinophil chemotactic chemokines (eotaxin, eotaxin-2, RANTES, monocyte chemoattractant protein-3 (MCP-3), and MCP-4), and C-C chemokine receptor 3 expression in bronchial biopsies from atopic and nonatopic (Intrinsic) asthmatics," *J. Immunol.* 1999, 163, 6321-6329.

Gavezzotti, "Are crystal structures predictable," *Acc. Chem. Res.*, 1994, 27, 309-314.

Vippagunta, et al. "Crystalline Solids," *Advanced Drug Delivery Reviews*, 2001, 48.3-26.

Berge, et al., "Pharmaceutical Salts," *J. Pharm. Sci.* 1977, 66, 1-19.

Iino, et al., "Molecular cloning and functional characterization of cynomolgus monkey (Macaca fascicularis) CC chemokine receptor, CCR3," Cytokine, 2002, 19, 276-286.

Office Action dated Apr. 17, 2012 from U.S. Appl. No. 12/764,249.

Notice of Allowance dated Jul. 27, 2012 from U.S. Appl. No. 12/764,249.

\* cited by examiner

2,5-DISUBSTITUTED ARYLSULFONAMIDE CCR3 ANTAGONISTS

CROSS REFERENCE TO RELATED APPLICATIONS

This application is a divisional application of U.S. application Ser. No. 12/764,249, filed on Apr. 21, 2010, which claims the benefit of priority to U.S. Provisional Patent Application No. 61/171,626, filed Apr. 22, 2009, the disclosure of each of which is incorporated herein by reference in its entirety.

FIELD

Provided herein are 2,5-disubstituted arylsulfonamides that are useful for modulating CCR3 activity, and pharmaceutical compositions thereof. Also provided herein are methods of their use for treating, preventing, or ameliorating one or more symptoms of a CCR3-mediated disorder, disease, or condition.

BACKGROUND

CC chemokine receptor 3 (CCR3) is a seven-transmembrane G protein-coupled receptor, which binds to a variety of C—C chemokines, including eotaxin (CCL11), eotaxin-3 (CCL26), MCP-3 (CCL7), MCP-4 (CCL13), and RANTES (CCL5). CCR3 is known to be a major chemokine receptor expressed on allergic inflammatory cells, including eosinophils, basophils, mast cells, and T helper 2-type CD4+ cells (Combadiere et al., *J. Biol. Chem.* 1995, 270, 16491-16494; Post et al., *J. Immunol.* 1995, 155, 5299-5305). Eosinophils have been implicated in the pathogenesis of a number of allergic diseases, such as bronchial asthma (Durham and Kay, *Clin. Allergy* 1985, 15, 411-418; Kroegel et al., *J. Allergy Clin. Immunol.* 1994, 93, 725-734), allergic rhinitis (Durham, *Clin. Exp. Allergy* 1998, 28 *Suppl.* 2, 11-16.), atopic dermatitis (Leung, *J. Allergy Clin. Immunol.* 1999, 104, S99-108), and eosinophilic gastroenteritis (Bischoff et al., *Am. J. Gastro.* 1999, 94, 3521-3529). It has been demonstrated that activated eosinophils release major basic protein (MBP), which blocks inhibitory M2 muscarinic receptors (M2Rs) on nerves, increasing acetylcholine release, and potentiating vagally mediated bronchoconstriction (Evans et al., *J. Clin. Invest.* 1997, 100, 2254-2262).

Numerous reports indicate that CCR3 plays important roles in allergic conditions. For example, it has been reported that, in both atopic and nonatopic asthma patients, there are increases in both mRNA and protein levels of CCR3 and its ligands, eotaxin, eotaxin-2, RANTES, and MCP-4 (Ying et al., *J. Immunol.* 1999, 99, 6321-6329). It has also been demonstrated that CCR3 gene deletion impairs eosinophil recruitment in an acute model of experimental asthma (Humbles et al., *Proc. Natl. Acad. Sci. USA* 2002, 99, 1479-1484; Ma et al., *J. Clin. Invest.* 2002, 109, 621-628; Pope et al., *J. Immunol.* 2005, 175, 5341-5350; Fulkerson et al., *Proc. Natl. Acad. Sci. USA* 2006, 103, 16418-16423). Furthermore, studies have shown that CCR3 antagonists, such as anti-CCR3 monoclonal antibodies, block binding of CCR3-ligands to either CCR3 transfectants or eosinophils, thus blocking chemotaxis of eosinophils induced by C—C chemokines, such as eotaxin, RANTES, or MCP-3 (Heath et al., *J. Clin. Invest.* 1997, 99, 178-184; Grimaldi et al., *J. Leukocyte Biol.* 1999, 65, 846-853; Justice et al., *Am. J. Physiol.* 2003, 284, L168-L178). Therefore, CCR3 antagonists are potentially useful for the treatment of inflammatory diseases, such as allergic rhinitis and allergic asthma. In addition, CCR3 antagonists are also potentially useful blocking infection of CCR3 expressing cells by some microorganisms, such as HIV, as CCR3 is known to be an entry co-receptor for some microorganisms.

SUMMARY OF THE DISCLOSURE

Provided herein is a 2,5-disubstituted arylsulfonamide of Formula Ia:

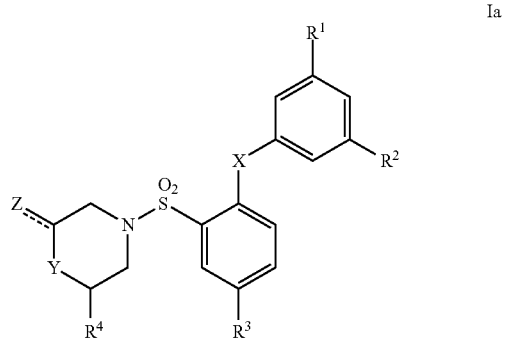

or a pharmaceutically acceptable salt, solvate, hydrate, stereoisomer or tautomer thereof;

wherein

X is S, SO, or $SO_2$;

Y and Z are (i) Y is $NR^5$; and Z is =O, $CO_2R^6$, or $C_{1-6}$ alkyl optionally substituted by aryl, hydroxy, carboxy, alkoxy, carbamoyl, or halo; or (ii) Y is $CH_2$, CHF, $CHCH_3$, O, S, or $SO_2$; and Z is hydrogen or $C_{1-6}$ alkyl optionally substituted by aryl, hydroxy, carboxy, alkoxy, carbamoyl, or halo;

$R^1$ and $R^2$ are independently halogen, $C_{1-6}$ alkyl, or $C_{1-6}$ haloalkyl;

$R^3$ is CN or $NO_2$;

$R^4$ is hydrogen or $C_{1-6}$ alkyl optionally substituted by aryl, hydroxy, carboxy, alkoxy, carbamoyl, or halo;

$R^5$ is hydrogen or $C_{1-6}$ alkyl; and $R^6$ is hydrogen or $C_{1-6}$ alkyl.

Also provided herein is a 2,5-disubstituted arylsulfonamide of Formula I:

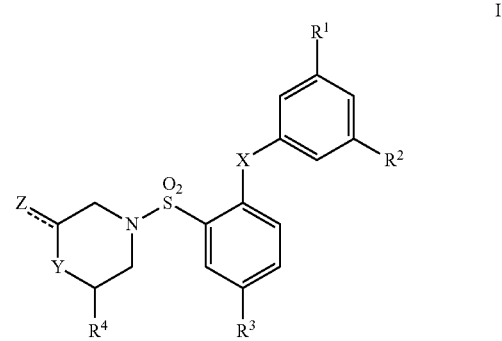

or a pharmaceutically acceptable salt, solvate, hydrate, stereoisomer or tautomer thereof; wherein X is S, SO, or $SO_2$;

Y and Z are
  (i) Y is $NR^5$; and Z is =O or $C_{1-6}$ alkyl optionally substituted by aryl, hydroxy, carboxy, alkoxy, carbamoyl, or halo; or
  (ii) Y is $CH_2$, CHF, $CHCH_3$, O, S, or $SO_2$; and Z is hydrogen or $C_{1-6}$ alkyl optionally substituted by aryl, hydroxy, carboxy, alkoxy, carbamoyl, or halo;

$R^1$ and $R^2$ are independently halogen, $C_{1-6}$ alkyl, or $C_{1-6}$ haloalkyl;

$R^3$ is CN or $NO_2$;

$R^4$ is hydrogen or $C_{1-6}$ alkyl optionally substituted by aryl, hydroxy, carboxy, alkoxy, carbamoyl, or halo; and $R^5$ is hydrogen or $C_{1-6}$ alkyl.

Also provided herein is a 2,5-disubstituted arylsulfonamide of Formula II, or a pharmaceutically acceptable salt, solvate, hydrate, stereoisomer, or tautomer thereof:

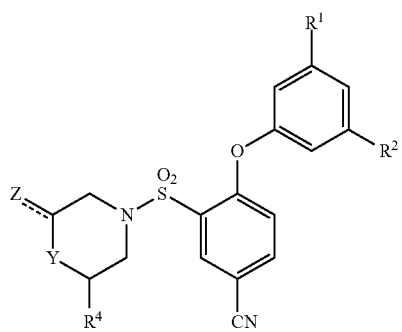

II

Y and Z are
  (i) Y is $NR^5$; and Z is =O or $C_{1-6}$ alkyl optionally substituted by aryl, hydroxy, carboxy, alkoxy, carbamoyl, or halo; or
  (ii) Y is $CH_2$, CHF, $CHCH_3$, O, S, or $SO_2$; and Z is hydrogen or $C_{1-6}$ alkyl optionally substituted by aryl, hydroxy, carboxy, alkoxy, carbamoyl, or halo;

$R^1$ and $R^2$ are independently halogen, $C_{1-6}$ alkyl, or $C_{1-6}$ haloalkyl;

$R^4$ is hydrogen or $C_{1-6}$ alkyl optionally substituted by aryl, hydroxy, carboxy, alkoxy, carbamoyl, or halo; and $R^5$ is hydrogen or $C_{1-6}$ alkyl;

with the proviso that when Y is $CH_2$, at least one of Z and $R^4$ is $C_{1-6}$ alkyl optionally substituted by aryl, hydroxy, carboxy, alkoxy, carbamoyl, or halo.

Also provided herein are pharmaceutical compositions comprising a compound disclosed herein, e.g., a compound of Formula Ia, Formula I, or Formula II, or a pharmaceutically acceptable salt, solvate, hydrate, stereoisomer or tautomer thereof, in combination with one or more pharmaceutically acceptable carriers or excipients.

Further provided herein is a method for modulating CCR3 activity, comprising contacting a CCR3 with a therapeutically effective amount of a compound disclosed herein, e.g., a compound of Formula Ia, Formula I, or Formula II, or a pharmaceutically acceptable salt, solvate, hydrate, stereoisomer or tautomer thereof.

Additionally provided herein is a method for treating, preventing, or ameliorating one or more symptoms of a CCR3-mediated disorder, disease, or condition in a subject, comprising administering to the subject a therapeutically effective amount of a compound disclosed herein, e.g., a compound of Formula Ia, Formula I or Formula II, or a pharmaceutically acceptable salt, solvate, hydrate, stereoisomer or tautomer thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st Edition, Lippincott Williams & Wilkins: Philadelphia, Pa., 2005; *Handbook of Pharmaceutical Excipients*, 5th Edition, Rowe et al., Eds., The Pharmaceutical Press and the American Pharmaceutical Association: 2005; and *Handbook of Pharmaceutical Additives*, 3rd Edition, Ash and Ash Eds., Gower Publishing Company: 2007; *Pharmaceutical Preformulation and Formulation*, Gibson Ed., CRC Press LLC: Boca Raton, Fla., 2004.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "alkyl" refers to a linear or branched saturated monovalent hydrocarbon radical, wherein the alkylene may optionally be substituted as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkenyl" refers to a linear or branched monovalent hydrocarbon radical, which contains one or more, in one embodiment, one to five, carbon-carbon double bonds. The alkenyl may be optionally substituted as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, carbon-carbon triple bonds. The alkynyl may be optionally substituted as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic saturated bridged and/or non-bridged monovalent hydrocarbon radical, which may be optionally substituted as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. In certain embodiments, heteroaryl may also be optionally substituted as described herein.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl, and 1,3,5-trithianyl. In certain embodiments, heterocyclic may also be optionally substituted as described herein.

The term "alkoxy" refers to an —OR radical, wherein R is, for example, alkyl, alkenyl, alkynyl, cycloalkyl, aryl, heteroaryl, or heterocyclyl, each as defined herein. Examples of alkoxy groups include, but are not limited to, methoxy, ethoxy, propoxy, n-propoxy, 2-propoxy, n-butoxy, isobutoxy, tert-butoxy, cyclohexyloxy, phenoxy, benzoxy, and 2-naphthyloxy. In certain embodiments, alkoxy may be optionally substituted as described herein. In certain embodiments, alkoxy is $C_{1-6}$ alkyl-oxy.

The term "halogen", "halide" or "halo" refers to fluorine, chlorine, bromine, and/or iodine.

The term "optionally substituted" is intended to mean that a group, such as an alkyl, alkenyl, alkynyl, cycloalkyl, aryl, heteroaryl, heterocyclyl, or alkoxy group, may be substituted with one or more substituents independently selected from, e.g., (a) alkyl, alkenyl, alkynyl, cycloalkyl, aryl, heteroaryl, and heterocyclyl, each optionally substituted with one or more, in one embodiment, one, two, three, or four, substituents Q; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more, in one embodiment, one, two, three, or four, substituents Q; or (iii) R$^b$ and R$^c$ together with the N atom to which they are attached form heterocyclyl, optionally substituted with one or more, in one embodiment, one, two, three, or four, substituents Q. As used herein, all groups that can be substituted are "optionally substituted," unless otherwise specified.

In one embodiment, each Q is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, heteroaryl, and heterocyclyl; and —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or (iii) R$^f$ and R$^g$ together with the N atom to which they are attached form heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "CCR3" refers to CC chemokine receptor 3 or a variant thereof, which is capable of mediating a cellular response to a variety of chemokines, including, but not limited to, eotaxin (CCL11), eotaxin-3 (CCL26), MCP-3 (CCL7), MCP-4 (CCL13), and RANTES (CCL5). CCR3 variants include proteins substantially homologous to a native CCR3, i.e., proteins having one or more naturally or non-naturally occurring amino acid deletions, insertions or substitutions (e.g., CCR3 derivatives, homologs and fragments), as compared to the amino acid sequence of a native CCR3. The amino acid sequence of a CCR3 variant is at least about 80% identical, at least about 90% identical, or at least about 95% identical to a native CCR3.

The term "CCR3 antagonist" refers to a compound that, e.g., partially or totally blocks, decreases, prevents, inhibits, or downregulates CCR3 activity. The term "CCR3 antagonist" also refers to a compound that binds to, delays the activation of, inactivates, or desensitizes a CCR3 receptor. A CCR3 antagonist may act by interfering with the interaction of a CCR3 receptor and its chemokine ligand, including, but not limited to, eotaxin (CCL11), eotaxin-3 (CCL26), MCP-3 (CCL7), MCP-4 (CCL13), and/or RANTES (CCL5).

The terms "CCR3-mediated disorder or disease" and "a condition, disorder or disease mediated by CCR3" refer to a condition, disorder, or disease characterized by inappropriate, e.g., less than or greater than normal, CCR3 activity. Inappropriate CCR3 functional activity might arise as the result of CCR3 expression in cells which normally do not express CCR3, increased CCR3 expression or degree of intracellular activation, leading to, e.g., inflammatory and immune-related disorders or diseases; or decreased CCR3 expression. A CCR3-mediated condition, disorder or disease may be completely or partially mediated by inappropriate CCR3 activity. In particular, a CCR3-mediated condition, disorder or disease is one in which modulation of a CCR3 receptor results in some effect on the underlying condition or disorder, e.g., a CCR3 antagonist or agonist results in some improvement in at least some of patients being treated.

Compounds

Provided herein are 2,5-disubstituted arylsulfonamides which are useful for modulating CCR3 activity. Also provided herein are pharmaceutical compositions which comprise the compounds and methods of use of the compounds and compositions for the treatment of a CCR3-mediated disorder, disease, or condition.

In one embodiment, provided herein is a 2,5-disubstituted arylsulfonamide of Formula Ia:

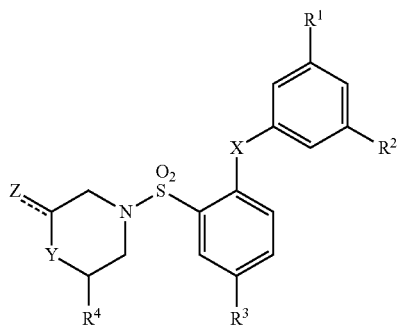

Ia or a pharmaceutically acceptable salt, solvate, hydrate, stereoisomer or tautomer thereof;
wherein
X is S, SO, or $SO_2$;
Y and Z are
(i) Y is $NR^5$; and Z is =O, $CO_2R^6$, or $C_{1-6}$ alkyl optionally substituted by aryl, hydroxy, carboxy, alkoxy, carbamoyl, or halo; or (ii) Y is $CH_2$, CHF, $CHCH_3$, O, S, or $SO_2$; and Z is hydrogen or $C_{1-6}$ alkyl optionally substituted by aryl, hydroxy, carboxy, alkoxy, carbamoyl, or halo;
$R^1$ and $R^2$ are independently halogen, $C_{1-6}$ alkyl, or $C_{1-6}$ haloalkyl;
$R^3$ is CN or $NO_2$;
$R^4$ is hydrogen or $C_{1-6}$ alkyl optionally substituted by aryl, hydroxy, carboxy, alkoxy, carbamoyl, or halo;
$R^5$ is hydrogen or $C_{1-6}$ alkyl; and
$R^6$ is hydrogen or $C_{1-6}$ alkyl.

In certain embodiments of Formula Ia, X is S. In certain embodiments of Formula Ia, X is SO. In certain embodiments of Formula Ia, X is $SO_2$.

In certain embodiments of Formula Ia, Y is $NR^5$. In embodiments of Formula Ia where Y is $NR^5$, Z is =O or $C_{1-6}$ alkyl optionally substituted. In one embodiment of Formula Ia where Y is $NR^5$, Z is $C_{1-6}$ alkyl optionally substituted by aryl, hydroxy, carboxy, alkoxy, carbamoyl, or halo. In one embodiment of Formula Ia where Y is $NR^5$, Z is —$CH_3$. In one embodiment of Formula Ia where Y is $NR^5$, Z is $CO_2R^6$. In one embodiment of Formula Ia where Y is $NR^5$ and Z is $CO_2R^6$, $R^6$ is $CH_3$. In one embodiment of Formula Ia where Y is $NR^5$, Z is $CO_2CH_3$. In another embodiment of Formula Ia where Y is $NR^5$, Z is =O. In various embodiments of Formula Ia where Y is $NR^5$, $R^5$ is hydrogen or $C_{1-6}$ alkyl. In certain embodiments of Formula Ia where Y is $NR^5$, $R^5$ is $C_{1-6}$ alkyl. In certain embodiments of Formula Ia where Y is $NR^5$, $R^5$ is hydrogen. In certain embodiments of Formula Ia where Y is $NR^5$, $R^5$ is methyl. In certain embodiments of Formula Ia where Y is $NR^5$, $R^5$ is isopropyl.

In certain embodiments of Formula Ia, Y is $CH_2$, CHF, $CHCH_3$, O, S, or $SO_2$. In embodiments of Formula Ia where Y is $CH_2$, CHF, $CHCH_3$, O, S, or $SO_2$, Z is hydrogen or $C_{1-6}$ alkyl optionally substituted. In certain embodiments of Formula Ia where Y is $CH_2$, CHF, $CHCH_3$, O, S, or $SO_2$, Z is hydrogen. In certain embodiments of Formula Ia where Y is $CH_2$, CHF, $CHCH_3$, O, S, or $SO_2$, Z is $C_{1-6}$ alkyl optionally substituted by aryl, hydroxy, carboxy, alkoxy, carbamoyl, or halo. In certain embodiments of Formula Ia where Y is $CH_2$, CHF, $CHCH_3$, O, S, or $SO_2$, Z is methyl. In certain embodiments of Formula Ia, Y is $CH_2$. In certain embodiments of Formula Ia, Y is CHF. In certain embodiments of Formula Ia, Y is $CHCH_3$. In certain embodiments of Formula Ia, Y is O. In certain embodiments of Formula Ia, Y is S. In certain embodiments of Formula Ia, Y is $SO_2$. I In certain embodiments of Formula Ia, $R^1$ is halogen, $C_{1-6}$ alkyl, or $C_{1-6}$ haloalkyl. In certain embodiments of Formula Ia, $R^1$ is halogen. In certain embodiments of Formula Ia, $R^1$ is fluoro or chloro. In certain embodiments of Formula Ia, $R^1$ is chloro. In certain embodiments of Formula Ia, $R^1$ is $C_{1-6}$ alkyl. In certain embodiments of Formula Ia, $R^1$ is methyl. In certain embodiments of Formula Ia, $R^1$ is $C_{1-6}$ haloalkyl. In certain embodiments of Formula Ia, $R^1$ is trifluoromethyl.

In certain embodiments of Formula Ia, $R^2$ is halogen, $C_{1-6}$ alkyl, or $C_{1-6}$ haloalkyl. In certain embodiments of Formula Ia, $R^2$ is halogen. In certain embodiments of Formula Ia, $R^2$ is fluoro or chloro. In certain embodiments of Formula Ia, $R^2$ is chloro. In certain embodiments of Formula Ia, $R^2$ is $C_{1-6}$ alkyl. In certain embodiments of Formula Ia, $R^2$ is methyl. In certain embodiments of Formula Ia, $R^2$ is $C_{1-6}$ haloalkyl. In certain embodiments of Formula Ia, $R^2$ is trifluoromethyl.

In certain embodiments of Formula Ia, $R^1$ and $R^2$ are different. In certain embodiments of Formula Ia, $R^1$ and $R^2$ are the same. In certain embodiments of Formula Ia, $R^1$ and $R^2$ are both chloro. In certain embodiments of Formula Ia, $R^1$ and $R^2$ are both methyl. In certain embodiments of Formula Ia, $R^1$ and $R^2$ are both trifluoromethyl.

In certain embodiments of Formula Ia, $R^3$ is cyano. In certain embodiments of Formula Ia, $R^3$ is nitro.

In certain embodiments of Formula Ia, $R^4$ is hydrogen or $C_{1-6}$ alky optionally substituted. In certain embodiments of Formula Ia, $R^4$ is hydrogen. In certain embodiments of Formula Ia, $R^4$ is $C_{1-6}$ alkyl optionally substituted by aryl, hydroxy, carboxy, alkoxy, carbamoyl, or halo. In certain embodiments of Formula Ia, $R^4$ is methyl.

In another embodiment, provided herein is a 2,5-disubstituted arylsulfonamide of Formula I or a pharmaceutically acceptable salt, solvate, hydrate, stereoisomer or tautomer thereof:

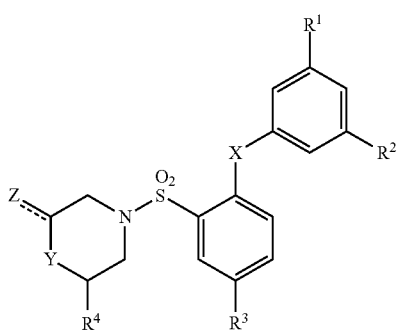

I wherein
X is S, SO, or $SO_2$;
Y and Z are
  (i) Y is $NR^5$; and Z is $=O$ or $C_{1-6}$ alkyl optionally substituted by aryl, hydroxy, carboxy, alkoxy, carbamoyl, or halo; or
  (ii) Y is $CH_2$, CHF, $CHCH_3$, O, S, or $SO_2$; and Z is hydrogen or $C_{1-6}$ alkyl optionally substituted by aryl, hydroxy, carboxy, alkoxy, carbamoyl, or halo;
$R^1$ and $R^2$ are independently halogen, $C_{1-6}$ alkyl, or $C_{1-6}$ haloalkyl;
$R^3$ is CN or $NO_2$;
$R^4$ is hydrogen or $C_{1-6}$ alkyl optionally substituted by aryl, hydroxy, carboxy, alkoxy, carbamoyl, or halo; and
$R^5$ is hydrogen or $C_{1-6}$ alkyl.

In certain embodiments of Formula I, X is S. In certain embodiments of Formula I, X is SO. In certain embodiments of Formula I, X is $SO_2$.

In certain embodiments of Formula I, Y is $NR^5$. In embodiments of Formula I where Y is $NR^5$, Z is $=O$ or $C_{1-6}$ alkyl optionally substituted. In one embodiment of Formula I where Y is $NR^5$, Z is $C_{1-6}$ alkyl optionally substituted by aryl, hydroxy, carboxy, alkoxy, carbamoyl, or halo. In one embodiment of Formula I where Y is $NR^5$, Z is $—CH_3$. In another embodiment of Formula I where Y is $NR^5$, Z is $=O$. In various embodiments of Formula I where Y is $NR^5$, $R^5$ is hydrogen or $C_{1-6}$ alkyl. In certain embodiments of Formula I where Y is $NR^5$, $R^5$ is $C_{1-6}$ alkyl. In certain embodiments of Formula I where Y is $NR^5$, $R^5$ is hydrogen. In certain embodiments of Formula I where Y is $NR^5$, $R^5$ is methyl. In certain embodiments of Formula I where Y is $NR^5$, $R^5$ is isopropyl.

In certain embodiments of Formula I, Y is $CH_2$, CHF, $CHCH_3$, O, S, or $SO_2$. In embodiments of Formula I where Y is $CH_2$, CHF, $CHCH_3$, O, S, or $SO_2$, Z is hydrogen or $C_{1-6}$ alkyl optionally substituted. In certain embodiments of Formula I where Y is $CH_2$, CHF, $CHCH_3$, O, S, or $SO_2$, Z is hydrogen. In certain embodiments of Formula I where Y is $CH_2$, CHF, $CHCH_3$, O, S, or $SO_2$, Z is $C_{1-6}$ alkyl optionally substituted by aryl, hydroxy, carboxy, alkoxy, carbamoyl, or halo. In certain embodiments of Formula I where Y is $CH_2$, CHF, $CHCH_3$, O, S, or $SO_2$, Z is methyl. In certain embodiments of Formula I, Y is $CH_2$. In certain embodiments of Formula I, Y is CHF. In certain embodiments of Formula I, Y is $CHCH_3$. In certain embodiments of Formula I, Y is O. In certain embodiments of Formula I, Y is S. In certain embodiments of Formula I, Y is $SO_2$. I In certain embodiments of Formula I, $R^1$ is halogen, $C_{1-6}$ alkyl, or $C_{1-6}$ haloalkyl. In certain embodiments of Formula I, $R^1$ is halogen. In certain embodiments of Formula I, $R^1$ is fluoro or chloro. In certain embodiments of Formula I, $R^1$ is chloro. In certain embodiments of Formula I, $R^1$ is $C_{1-6}$ alkyl. In certain embodiments of Formula I, $R^1$ is methyl. In certain embodiments of Formula I, $R^1$ is $C_{1-6}$ haloalkyl. In certain embodiments of Formula I, $R^1$ is trifluoromethyl.

In certain embodiments of Formula I, $R^2$ is halogen, $C_{1-6}$ alkyl, or $C_{1-6}$ haloalkyl. In certain embodiments of Formula I, $R^2$ is halogen. In certain embodiments of Formula I, $R^2$ is fluoro or chloro. In certain embodiments of Formula I, $R^2$ is chloro. In certain embodiments of Formula I, $R^2$ is $C_{1-6}$ alkyl. In certain embodiments of Formula I, $R^2$ is methyl. In certain embodiments of Formula I, $R^2$ is $C_{1-6}$ haloalkyl. In certain embodiments of Formula I, $R^2$ is trifluoromethyl.

In certain embodiments of Formula I, $R^1$ and $R^2$ are different. In certain embodiments of Formula I, $R^1$ and $R^2$ are the same. In certain embodiments of Formula I, $R^1$ and $R^2$ are both chloro. In certain embodiments of Formula I, $R^1$ and $R^2$ are both methyl. In certain embodiments of Formula I, $R^1$ and $R^2$ are both trifluoromethyl.

In certain embodiments of Formula I, $R^3$ is cyano. In certain embodiments of Formula I, $R^3$ is nitro.

In certain embodiments of Formula I, $R^4$ is hydrogen or $C_{1-6}$ alky optionally substituted. In certain embodiments of Formula I, $R^4$ is hydrogen. In certain embodiments of Formula I, $R^4$ is $C_{1-6}$ alkyl optionally substituted by aryl, hydroxy, carboxy, alkoxy, carbamoyl, or halo. In certain embodiments of Formula I, $R^4$ is methyl.

In another embodiment, provided herein is a 2,5-disubstituted arylsulfonamide of Formula II, or a pharmaceutically acceptable salt, solvate, hydrate, stereoisomer, or tautomer thereof:

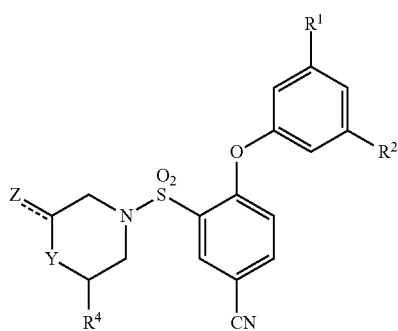

II wherein
Y and Z are
  (i) Y is $NR^5$; and Z is $=O$ or $C_{1-6}$ alkyl optionally substituted by aryl, hydroxy, carboxy, alkoxy, carbamoyl, or halo; or
  (ii) Y is $CH_2$, CHF, $CHCH_3$, O, S, or $SO_2$; and Z is hydrogen or $C_{1-6}$ alkyl optionally substituted by aryl, hydroxy, carboxy, alkoxy, carbamoyl, or halo;

$R^1$ and $R^2$ are independently halogen, $C_{1-6}$ alkyl, or $C_{1-6}$ haloalkyl;

$R^4$ is hydrogen or $C_{1-6}$ alkyl optionally substituted by aryl, hydroxy, carboxy, alkoxy, carbamoyl, or halo;

$R^5$ is hydrogen or $C_{1-6}$ alkyl;

with the proviso that when Y is $CH_2$, at least one of Z and $R^4$ is $C_{1-6}$ alkyl optionally substituted by aryl, hydroxy, carboxy, alkoxy, carbamoyl, or halo.

In certain embodiments of Formula II, Y is $NR^5$. In embodiments of Formula II where Y is $NR^5$, Z is =O or $C_{1-6}$ alkyl optionally substituted. In one embodiment of Formula II where Y is $NR^5$, Z is $C_{1-6}$ alkyl optionally substituted by aryl, hydroxy, carboxy, alkoxy, carbamoyl, or halo. In one embodiment of Formula II where Y is $NR^5$, Z is —$CH_3$. In another embodiment of Formula II where Y is $NR^5$, Z is =O. In various embodiments of Formula II where Y is $NR^5$, $R^5$ is hydrogen or $C_{1-6}$ alkyl. In certain embodiments of Formula II where Y is $NR^5$, $R^5$ is $C_{1-6}$ alkyl. In certain embodiments of Formula II where Y is $NR^5$, $R^5$ is hydrogen. In certain embodiments of Formula II where Y is $NR^5$, $R^5$ is methyl. In certain embodiments of Formula II where Y is $NR^5$, $R^5$ is isopropyl.

In certain embodiments of Formula II, Y is $CH_2$, CHF, $CHCH_3$, O, S, or $SO_2$. In embodiments of Formula II where Y is $CH_2$, CHF, $CHCH_3$, O, S, or $SO_2$, Z is hydrogen or $C_{1-6}$ alkyl optionally substituted. In certain embodiments of Formula II where Y is $CH_2$, CHF, $CHCH_3$, O, S, or $SO_2$, Z is hydrogen. In certain embodiments of Formula II where Y is $CH_2$, CHF, $CHCH_3$, O, S, or $SO_2$, Z is $C_{1-6}$ alkyl optionally substituted by aryl, hydroxy, carboxy, alkoxy, carbamoyl, or halo. In certain embodiments of Formula II where Y is $CH_2$, CHF, $CHCH_3$, O, S, or $SO_2$, Z is methyl. In certain embodiments of Formula II, Y is $CH_2$. In embodiments of Formula II where Y is $CH_2$, at least one of Z and $R^4$ is $C_{1-6}$ alkyl optionally substituted by aryl, hydroxy, carboxy, alkoxy, carbamoyl, or halo. In certain embodiments of Formula II, Y is CHF. In certain embodiments of Formula II, Y is $CHCH_3$. In certain embodiments of Formula II, Y is O. In certain embodiments of Formula II, Y is S. In certain embodiments of Formula II, Y is $SO_2$.

In certain embodiments of Formula II, $R^1$ is halogen, $C_{1-6}$ alkyl, or $C_{1-6}$ haloalkyl. In certain embodiments of Formula II, $R^1$ is halogen. In certain embodiments of Formula II, $R^1$ is fluoro or chloro. In certain embodiments of Formula II, $R^1$ is chloro. In certain embodiments of Formula II, $R^1$ is $C_{1-6}$ alkyl. In certain embodiments of Formula II, $R^1$ is methyl. In certain embodiments of Formula II, $R^1$ is $C_{1-6}$ haloalkyl. In certain embodiments of Formula II, $R^1$ is trifluoromethyl.

In certain embodiments of Formula II, $R^2$ is halogen, $C_{1-6}$ alkyl, or $C_{1-6}$ haloalkyl. In certain embodiments of Formula II, $R^2$ is halogen. In certain embodiments of Formula II, $R^2$ is fluoro or chloro. In certain embodiments of Formula II, $R^2$ is chloro. In certain embodiments of Formula II, $R^2$ is $C_{1-6}$ alkyl. In certain embodiments of Formula II, $R^2$ is methyl. In certain embodiments of Formula II, $R^2$ is $C_{1-6}$ haloalkyl. In certain embodiments of Formula II, $R^2$ is trifluoromethyl.

In certain embodiments of Formula II, $R^1$ and $R^2$ are different. In certain embodiments of Formula II, $R^1$ and $R^2$ are the same. In certain embodiments of Formula II, $R^1$ and $R^2$ are both chloro. In certain embodiments of Formula II, $R^1$ and $R^2$ are both methyl. In certain embodiments of Formula II, $R^1$ and $R^2$ are both trifluoromethyl.

In certain embodiments of Formula II, $R^4$ is hydrogen or $C_{1-6}$ alkyl optionally substituted. In certain embodiments of Formula II, $R^4$ is hydrogen. In certain embodiments of Formula II, $R^4$ is $C_{1-6}$ alkyl optionally substituted by aryl, hydroxy, carboxy, alkoxy, carbamoyl, or halo. In certain embodiments of Formula II, $R^4$ is methyl.

In certain embodiments, provided herein is a compound selected from the group consisting of:

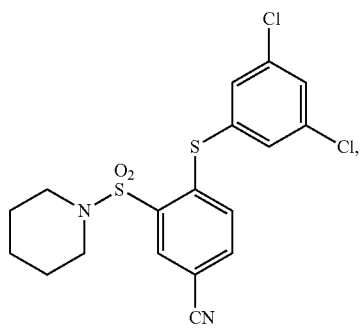

1

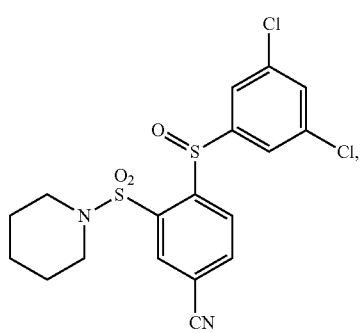

2

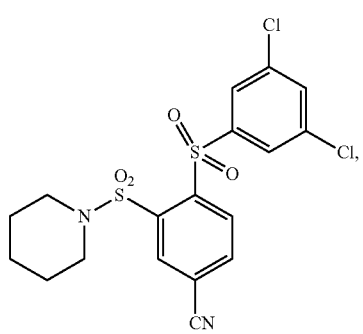

3

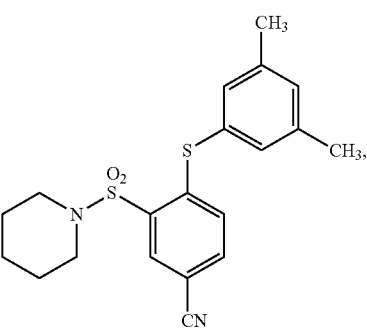

4

15
-continued
5
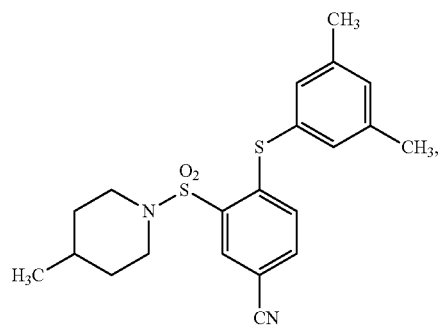
6
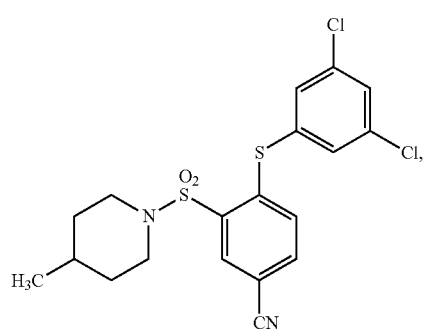
7
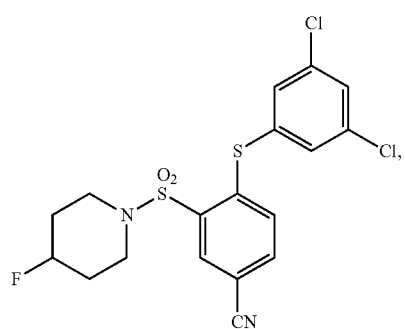
8
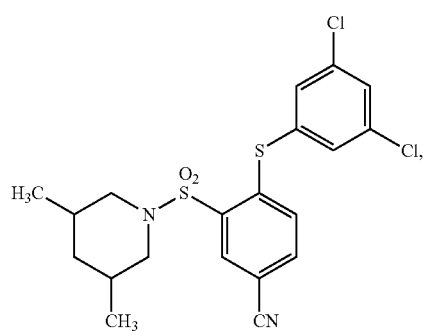
9
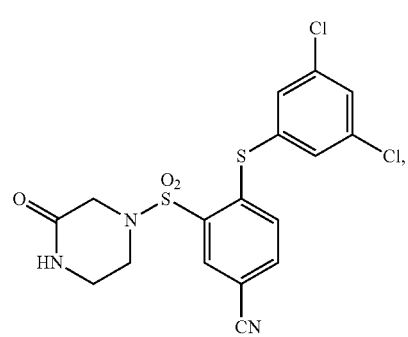
16
-continued
10
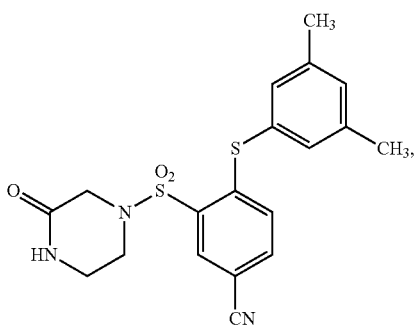
11
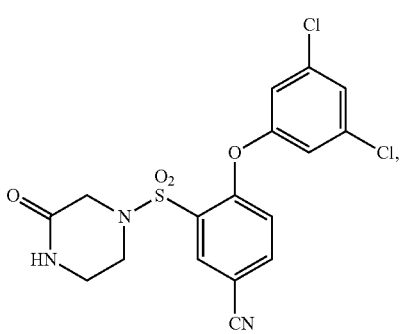
12
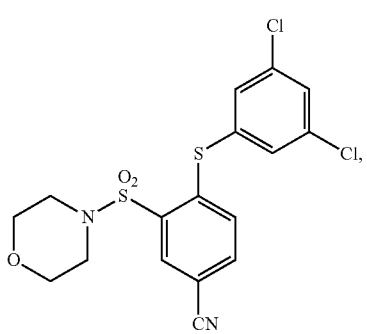
13
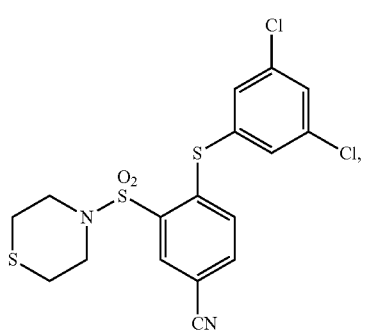
14
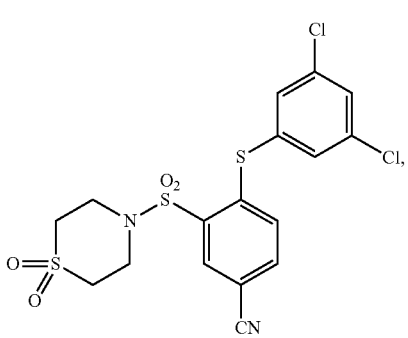

-continued
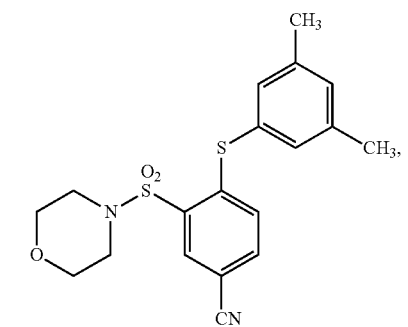
15
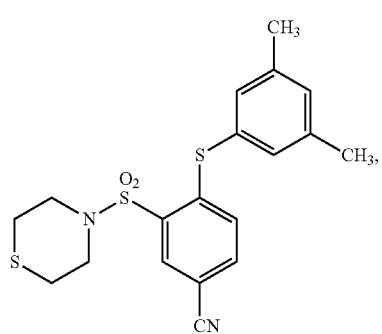
16
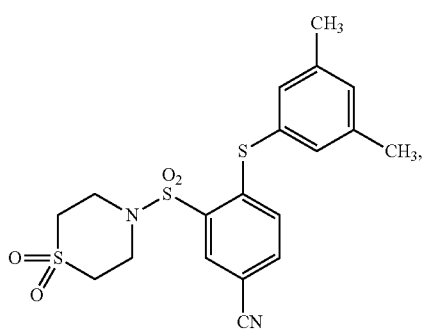
17
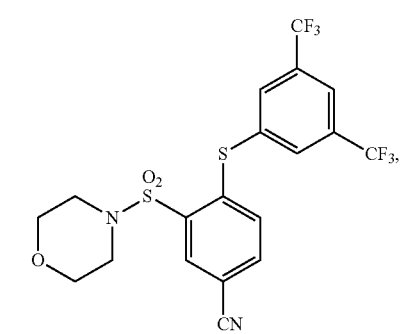
18
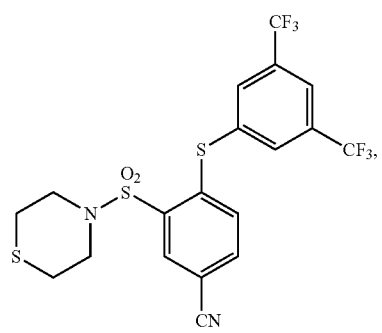
19
-continued
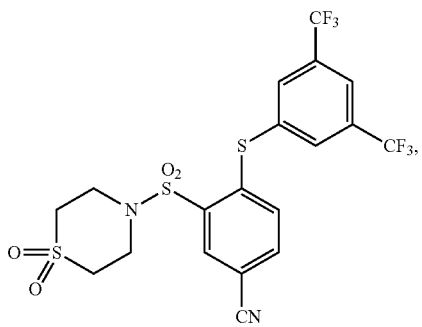
20
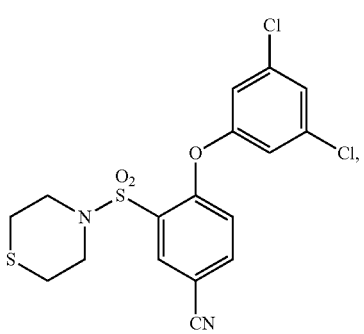
21
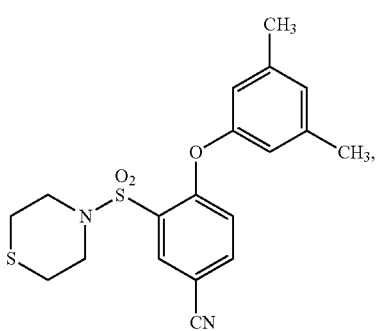
22
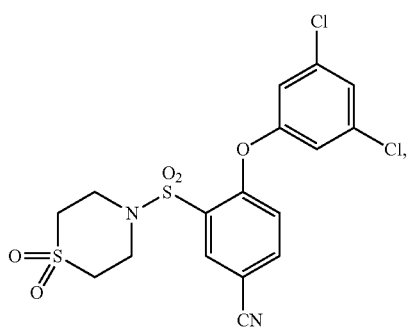
23
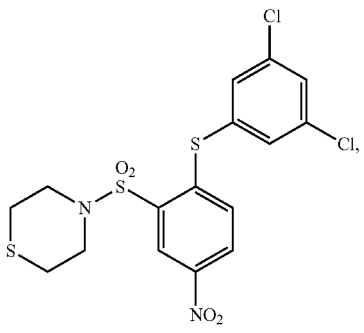
24

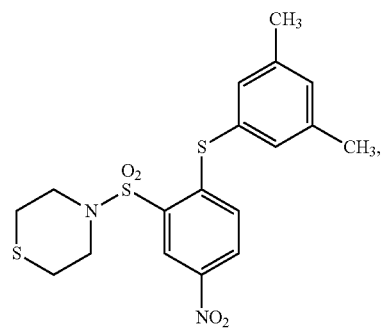

25

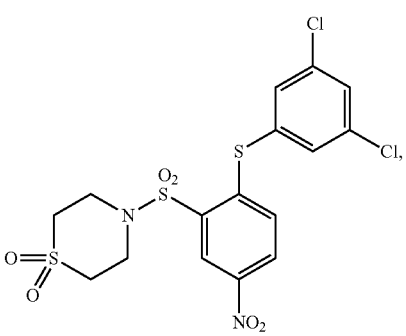

30

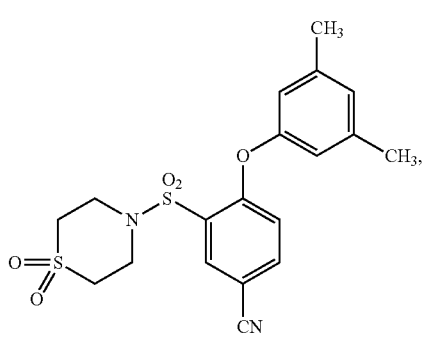

26

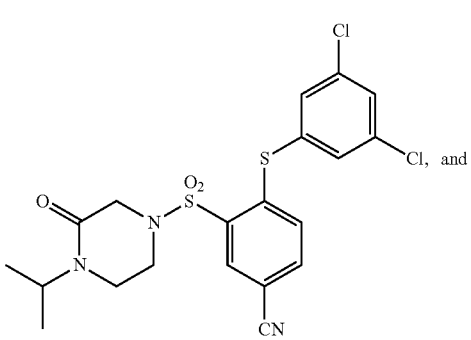

31

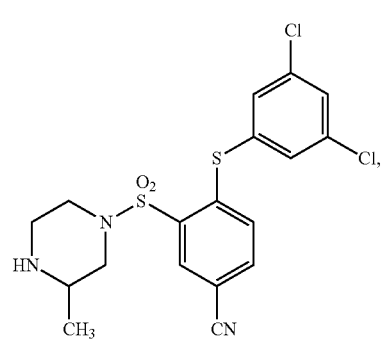

27

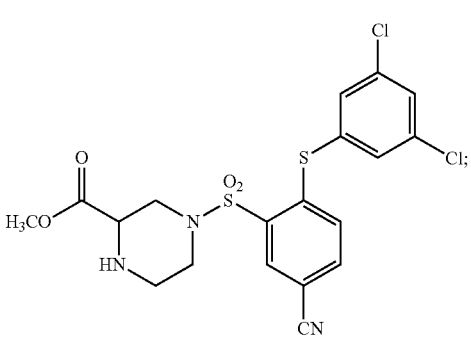

32

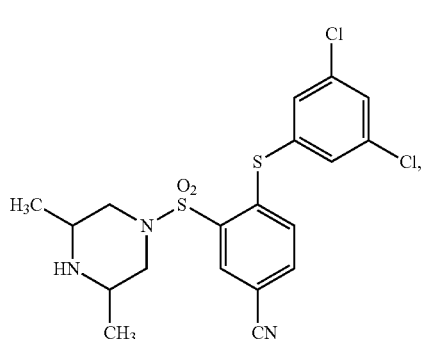

28

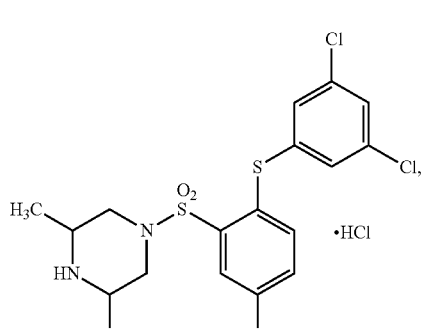

29 and pharmaceutically acceptable salts, solvates, hydrates, stereoisomers, and tautomers thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible via a low energy barrier, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

The compounds provided herein may also be isotopically labeled at one or more sites in the molecules. In certain embodiments, the compounds provided herein may be selectively deuterated at a site which retards the rate of metabolic deactivation to, for example, increase the circulation half-life in vivo.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I or Formula II and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs*, 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

The compounds provided herein can be prepared, isolated, or obtained by any method known to one of skill in the art. For an example, a compound of Formula Ia or Formula I can be prepared by a synthetic scheme as illustrated in Scheme 1. In the first step, a nitrobenzene reacts with a 1,3,5-trisubstituted benzene in the presence of base (such as potassium carbonate or sodium hydride) via an aromatic substitution reaction. The product nitroaryl is reduced with a reducing agent (such as $TiCl_2$ or sodium hydrosulfite) to an aniline, which is then converted to a sulfonyl chloride via a Sandmeyer reaction. A compound of Formula Ia or Formula I is formed by reacting the sulfonyl chloride with an appropriate nitrogen-containing heterocycle in the presence of a base, such as triethylamine.

A compound of Formula II can be prepared by a synthetic scheme analogous to that illustrated in Scheme 1.

A compound of Formula Ia or Formula I can also be prepared by the synthetic scheme illustrated in Scheme 2. In the first step, an aniline is first converted to a sulfonyl chloride via a Sandmeyer reaction. Subsequently, the sulfonyl chloride is reacted with an appropriate nitrogen-containing heterocycle in the presence of a base, such as triethylamine, to form a 2-chloro-5-substituted sulfonamide, which is then reacted with an appropriate 1,3,5-trisubstituted benzene by aromatic substitution reaction in the presence of a base, such as potassium carbonate or sodium hydride, to form a compound of Formula Ia or Formula I.

Scheme 1

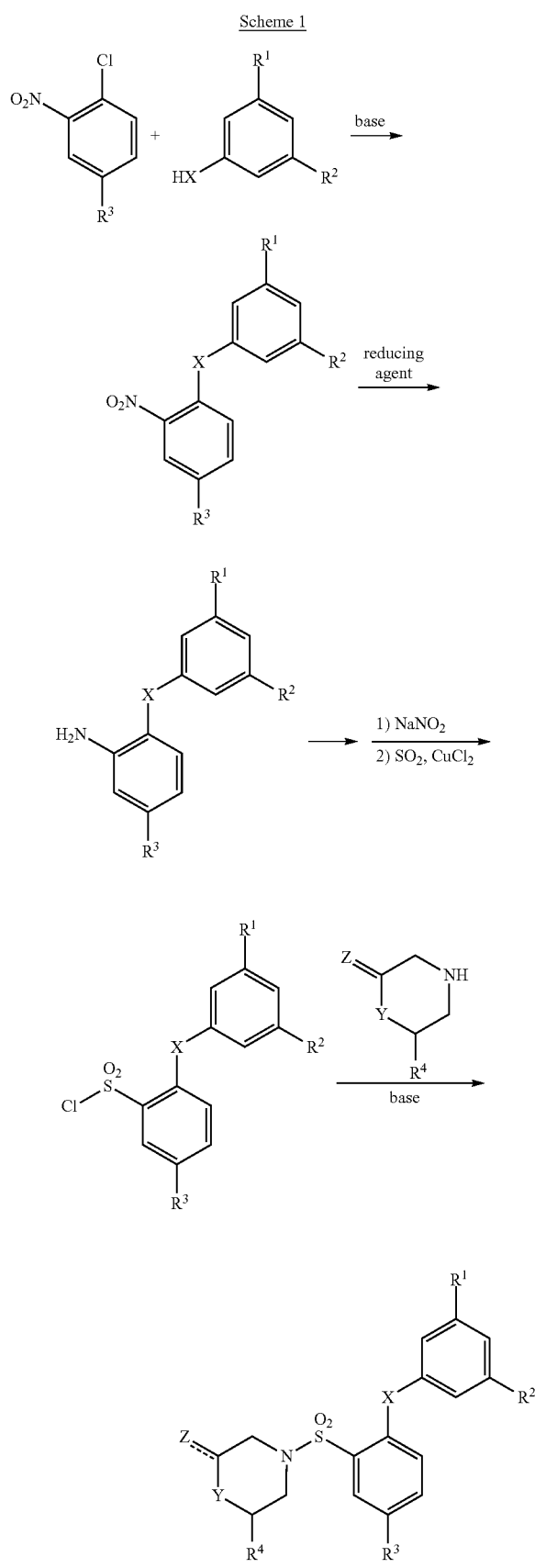

A compound of Formula II can be prepared by a synthetic scheme analogous to that illustrated in Scheme 2.

Scheme 2

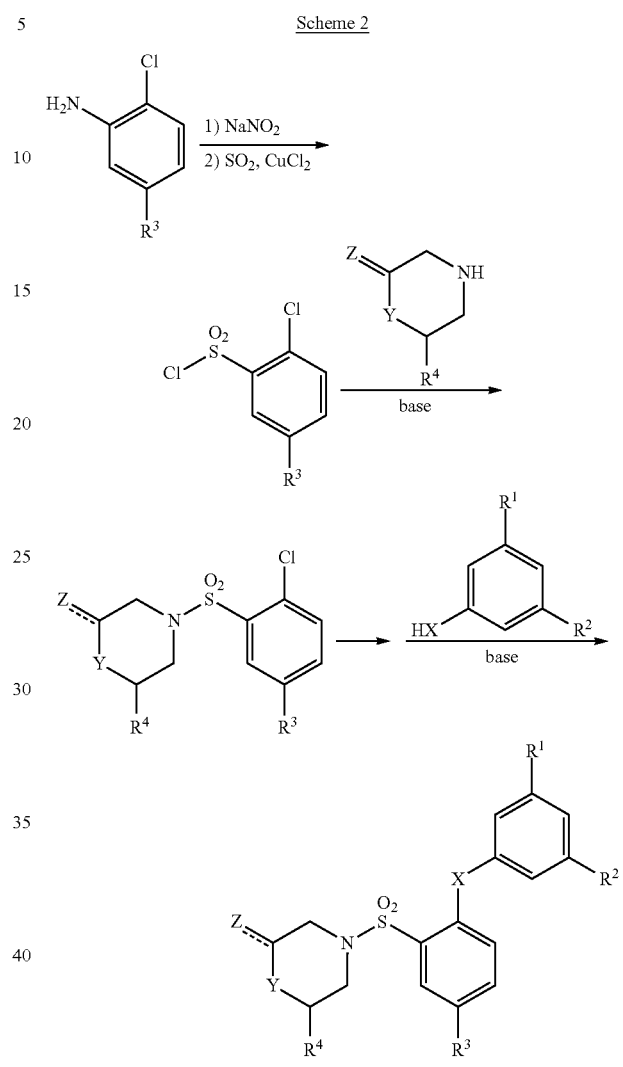

Pharmaceutical Compositions

Provided herein are pharmaceutical compositions comprising a compound provided herein, e.g., a compound of Formula Ia, Formula I, or Formula II, or a pharmaceutically acceptable salt, solvate, hydrate, stereoisomer or tautomer thereof, as an active ingredient; in combination with a pharmaceutically acceptable vehicle, carrier, diluent, or excipient, or a mixture thereof.

The compound provided herein may be administered alone, or in combination with one or more other compounds provided herein. The pharmaceutical compositions that comprise a compound provided herein, e.g., a compound of Formula Ia, Formula I, or Formula II, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Deliver Technology, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise a compound provided herein, e.g., a compound of Formula Ia, Formula I, or Formula II, or a pharmaceutically acceptable salt, solvate, hydrate, stereoisomer or tautomer thereof, and one or more pharmaceutically acceptable excipients or carriers.

In another embodiment, the pharmaceutical compositions are provided in a dosage form for parenteral administration, which comprise a compound provided herein, e.g., a compound of Formula Ia, Formula I, or Formula II, or a pharmaceutically acceptable salt, solvate, hydrate, stereoisomer or tautomer thereof, and one or more pharmaceutically acceptable excipients or carriers.

In yet another embodiment, the pharmaceutical compositions are provided in a dosage form for topical administration, which comprise a compound provided herein, e.g., a compound of Formula Ia, Formula I, or Formula II, or a pharmaceutically acceptable salt, solvate, hydrate, stereoisomer or tautomer thereof, and one or more pharmaceutically acceptable excipients or carriers; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, troches, lozenges, pastilles, cachets, pellets, medicated chewing gum, bulk powders, effervescent or non-effervescent powders or granules, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN®20), polyoxyethylene sorbitan monooleate 80 (TWEEN®80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein can be formulated as immediate or modified release dosage forms, including delayed-, sustained, pulsed-, controlled, targeted-, and programmed-release forms.

The pharmaceutical compositions provided herein can be co-formulated with other active ingredients which do not impair the desired therapeutic action, or with substances that supplement the desired action.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein can be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein can be formulated as immediate or modified release dosage forms, including delayed-, sustained, pulsed-, controlled, targeted-, and programmed-release forms.

The pharmaceutical compositions can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration can further comprise a suitable flavor, such as menthol and levomenthol, or sweeteners, such as saccharin or saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form can be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided is a method of treating, preventing, or ameliorating one or more symptoms of a disorder, disease, or condition associated with CCR3 in a subject, which comprises administering to the subject a therapeutically effective amount of a compound provided herein, e.g., a compound of Formula Ia, Formula I, or Formula II, or a pharmaceutically acceptable salt, solvate, hydrate, stereoisomer or tautomer thereof. In one embodiment, the subject is a mammal. In another embodiment, the subject is a human.

In another embodiment, provided is a method of treating, preventing, or ameliorating one or more symptoms of a disorder, disease, or condition responsive to the modulation of CCR3 activity in a subject, comprising administering to the subject a therapeutically effective amount of a compound provided herein, e.g., a compound of Formula Ia, Formula I, or Formula II, or a pharmaceutically acceptable salt, solvate, hydrate, stereoisomer or tautomer thereof. In one embodiment, the subject is a mammal. In another embodiment, the subject is a human.

In yet another embodiment, provided is a method of treating, preventing, or ameliorating one or more symptoms of a disorder, disease, or condition mediated by a CCR3 receptor in a subject, comprising administering to the subject a therapeutically effective amount of a compound provided herein, e.g., a compound of Formula Ia, Formula I, or Formula II, or a pharmaceutically acceptable salt, solvate, hydrate, stereoisomer or tautomer thereof. In one embodiment, the subject is a mammal. In another embodiment, the subject is a human.

In yet another embodiment, provided is a method for treating, preventing, or ameliorating one or more symptoms of an eosinophil-related disorder, disease, or condition in a subject, comprising administering to the subject a therapeutically effective amount of a compound provided herein, e.g., a compound of Formula Ia, Formula I, or Formula II, or a pharmaceutically acceptable salt, solvate, hydrate, stereoisomer or tautomer thereof. In one embodiment, the subject is a mammal. In another embodiment, the subject is a human.

In yet another embodiment, provided is a method for treating, preventing, or ameliorating one or more symptoms of a basophil-related disorder, disease, or condition in a subject, comprising administering to a subject, a therapeutically effective amount of a compound provided herein, e.g., a compound of Formula Ia, Formula I, or Formula II, or a pharmaceutically acceptable salt, solvate, hydrate, stereoisomer or tautomer thereof. In one embodiment, the subject is a mammal. In another embodiment, the subject is a human.

In yet another embodiment, provided is a method for treating, preventing, or ameliorating one or more symptoms of a mast cell-related disorder, disease, or condition in a subject, comprising administering to a subject a therapeutically effective amount of a compound provided herein, e.g., a compound of Formula Ia, Formula I, or Formula II, or a pharmaceutically acceptable salt, solvate, hydrate, stereoisomer or tautomer thereof. In one embodiment, the subject is a mammal. In another embodiment, the subject is a human.

In yet another embodiment, provided is a method for treating, preventing, or ameliorating one or more symptoms of an inflammatory disease in a subject, comprising administering to the subject a therapeutically effective amount of a compound provided herein, e.g., a compound of Formula Ia, Formula I, or Formula II, or a pharmaceutically acceptable salt, solvate, hydrate, stereoisomer or tautomer thereof. In one embodiment, the subject is a mammal. In another embodiment, the subject is a human.

The disorders, diseases, or conditions treatable with a compound provided herein, e.g., a compound of Formula Ia, Formula I, or Formula II, or a pharmaceutically acceptable salt, solvate, hydrate, stereoisomer or tautomer thereof, include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the disorder, disease, or condition is selected from the group consisting of asthma, allergic asthma, exercise induced asthma, allergic rhinitis, perennial allergic rhinitis, seasonal allergic rhinitis, atopic dermatitis, contact hypersensitivity, contact dermatitis, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematous, psoriasis, acne, multiple sclerosis, allograft rejection, reperfusion injury, chronic obstructive pulmonary disease, Churg-Strauss syndrome, sinusitis, basophilic leukemia, chronic urticaria, basophilic leukocytosis, psoriasis, eczema, COPD (chronic obstructive pulmonary disorder), arthritis, rheumatoid arthritis, psoriatic arthritis, and osteoarthritis.

In certain embodiments, the disorder, disease, or condition is asthma, exercise induced asthma, allergic rhinitis, atopic dermatitis, chronic obstructive plumonary disease, or allergic conjunctivitis.

In certain embodiments, the disorder, disease, or condition is an inflammatory or immunoregulatory disease. In certain embodiments, the disorder, disease, or condition is asthma, rhinitis, an allergic disease, or an autoimmune pathology. In certain embodiments, the disorder, disease, or condition is HIV, lung granuloma, or Alsheimer's disease.

In various embodiments, the methods for treating the above-mentioned disorders, diseases, or conditions comprise treatment of a subject with a pharmaceutical composition comprising a compound provided herein, e.g., a compound of Formula I or Formula II, or a pharmaceutically acceptable salt, solvate, hydrate, stereoisomer or tautomer thereof, in combination with one or more pharmaceutically acceptable excipients or carriers.

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, or other conditions, disorders or diseases associated with a CCR3 receptor, an appropriate dosage level generally is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day. In certain embodiments, the dosage level is ranging from about 0.001 to about 100 mg/kg per day. In certain embodiments, the dosage level is ranging from about 0.01 to about 75 mg/kg per day. In certain embodiments, the dosage level is ranging from about 0.1 to about 50 mg/kg per day. In certain embodiments, the dosage level is ranging from about 0.5 to about 25 mg/kg per day. In certain embodiments, the dosage level is ranging from about 1 to about 20 mg/kg per day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also provided herein are methods of modulating CCR3 activity, comprising contacting a CCR3 receptor with a compound provided herein, e.g., a compound of Formula Ia, Formula I, or Formula II, including an enantiomer, a mixture of enantiomers, a mixture of two or more diastereomers, a tautomer, or a mixture of two or more tautomers thereof or a pharmaceutically acceptable salt, solvate, hydrate, or prodrug thereof. In one embodiment, the CCR3 receptor is expressed by a cell.

The compounds provided herein, e.g., a compound of Formula Ia, Formula I, or Formula II, or a pharmaceutically acceptable salt, solvate, hydrate, stereoisomer or tautomer thereof, can also be combined or used in combination with other agents useful in the treatment, prevention, or amelioration of one or more symptoms of the disorders, diseases, or conditions for which the compounds provided herein are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, infectious diseases, and those pathologies noted above.

In certain embodiments, the compounds provided herein can be combined with one or more steroidal drugs known in the art, including, but not limited to the group including, aldosterone, beclometasone, betamethasone, deoxycorticosterone acetate, fludrocortisone, hydrocortisone (cortisol), prednisolone, prednisone, methylprednisolone, dexamethasone, and triamcinolone.

In certain embodiments, the compounds provided herein can be combined with one or more antibacterial agents known in the art, including, but not limited to the group including amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacin, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds provided herein can be combined with one or more antifungal agents known in the art, including, but not limited to the group including amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

In certain embodiments, the compounds provided herein can be combined with one or more anticoagulants known in the art, including, but not limited to the group including acenocoumarol, argatroban, bivalirudin, lepirudin, fondaparinux, heparin, phenindione, warfarin, and ximelagatran.

In certain embodiments, the compounds provided herein can be combined with one or more thrombolytics known in the art, including, but not limited to the group including anistreplase, reteplase, t-PA (alteplase activase), streptokinase, tenecteplase, and urokinase.

In certain embodiments, the compounds provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

In certain embodiments, the compounds provided herein can be combined with one or more antiplatelet agents known in the art, including, but not limited to, abciximab, cilostazol, clopidogrel, dipyridamole, ticlopidine, and tirofibin.

The compounds provided herein can also be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y (AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporine; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Such other agents, or drugs, can be administered, by a route and in an amount commonly used therefor, simultaneously or sequentially with the compounds provided herein, e.g., a compound of Formula Ia, Formula I, or Formula II, including a single enantiomer, a mixture of enantiomers, or a mixture of diastereomers thereof; or a pharmaceutically acceptable salt, solvate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

The weight ratio of a compound provided herein to the second active ingredient can be varied, and will depend upon the effective dose of each ingredient. Generally, an effective dose of each will be used. Thus, for example, when a compound provided herein is combined with a NSAID, the weight ratio of the compound to the NSAID can range from about 1,000:1 to about 1:1,000, or about 200:1 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, e.g., a compound of Formula Ia, Formula I, or Formula II, or a pharmaceutically acceptable salt, solvate, hydrate, stereoisomer or tautomer thereof.

In certain embodiments, the kit includes a container comprising a dosage form of the compound provided herein, e.g., a compound of Formula Ia, Formula I, or Formula II, or a pharmaceutically acceptable salt, solvate, hydrate, stereoisomer or tautomer thereof, in a container comprising one or more other therapeutic agent(s) described herein.

Kits provided herein can further include devices that are used to administer the active ingredients. Examples of such devices include, but are not limited to, syringes, needleless injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); nM (nanomolar); eq. (equivalent); Hz (Hertz); MHz (megahertz); mmol (millimoles); hr or hrs (hours); min (minutes); MS (mass spectrometry); ESI (electrospray ionization); TLC (thin layer chromatography); $R_t$ (retention time); $SiO_2$ (silica); THF (tetrahydrofuran); $CDCl_3$ (deuterated chloroform); DCM (dichloromethane); DMF (dimethyformamide); DMSO (dimethylsulfoxide); EtOAc (ethyl acetate); $CHCl_3$ (chloroform); DMF (N,N-dimethylformamide); MeOH (methanol); HCl (hydrochloric acid); LiOH (lithium hydroxide); $MgSO_4$ (magnesium sulfate); NaH (sodium hydride); NaOH (sodium hydroxide); $NaHCO_3$ (sodium bicarbonate); DIPEA (N,N-diisopropylethylamine); TEA (triethylamine); DBU (1,8-diazabicyclo[5.4.0]undec-7-ene); CDI (carbonyldiimidazole); TBTU (O-(benzotriazol-1-yl)-N,N,N',N'-tetramethyluronium tetrafluoroborate); Me (methyl); Et (ethyl); tBu (tert-butyl); Boc (tert-butoxylcarbony); Bn (benzyl); TsO (tosylate); DIAD (diisopropylazodicarboxylate), DEAD (diethylazodicarboxylate), $PPh_3$ (triphenylphosphine), PNBA (p-nitrobenzoic acid), and PNB (p-nitrobenzoyl).

For all of the following examples, standard work-up and purification methods known to those skilled in the art can be utilized. Unless otherwise indicated, all temperatures are expressed in ° C. (degrees Centigrade). All reactions were conducted at room temperature unless otherwise noted. Synthetic methodologies illustrated herein are intended to exemplify the applicable chemistry through the use of specific examples and are not indicative of the scope of the disclosure.

Example 1

Preparation of Compound 9

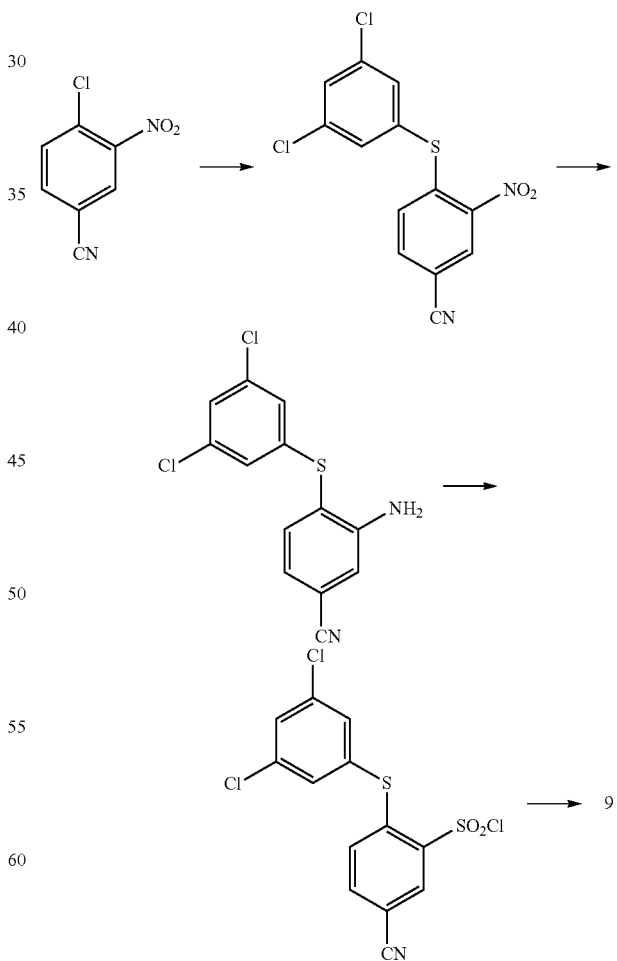

1) Preparation of 4-(3,5-dichlorophenylthio)-3-nitrobenzonitrile—3,5-Dichlorothiophenol (11.77 g, 65.74 mmol)

was dissolved in THF (80 mL), chilled in an ice bath and NaH (2.629 g, 109.56 mmol) was added. The thus obtained reaction mixture was stirred for 5 minutes before the introduction of 4-chloro-3-nitrobenzonitrile (10 g, 54.78 mmol), then stirred an additional 15 minutes before warming to room temperature. After 3 days, the reaction mixture was condensed in vacuo to remove the organic solvent. The resulting suspension was filtered and the filtered solids were rinsed with water to furnish the product as a yellow powder. (17.2 g, 86.5% HPLC purity, 96.6% yield). $^1$H-NMR: (500 MHz, DMSO-$d_6$) 8.77 (d, J=1 Hz, 1H), 7.99 (dd, $J_1$=8 Hz, $J_2$=2 Hz, 1H), 7.89 (t, $J_1$=$J_2$=1 Hz, 1H), 7.80 (d, J=2 Hz, 2H), 7.13 (d, J=9 Hz, 1H).

2) Preparation of 4-(3,5-dichlorophenylthio)-3-aminobenzonitrile—Sodium hydrosulfite (35.000 g, 201.02 mmol) was dissolved in minimal water (150 mL), to which was added a solution of 4-(3,5-dichlorophenylthio)-3-nitrobenzonitrile (17.2 g, 52.90 mmol) in THF (200 mL). The thus obtained reaction mixture was heated to and maintained at 90° C. for 18 h, after which the volatiles were removed in vacuo. The separated solids were collected by suction and rinsed with water to furnish the product as a yellow powder. (15.387 g, 93.3% purity by HPLC, 98.5% yield). $^1$H-NMR: (500 MHz, DMSO-$d_6$) 7.51 (d, J=8 Hz, 1H), 7.43 (t, $J_1$=$J_2$=1 Hz, 1H), 7.14 (d, J=1 Hz, 1H), 7.07 (d, J=1 Hz, 2H), 6.96 (dd, $J_1$=8 Hz, $J_2$=2 Hz, 1H), 6.02 (s, 2H).

3) Preparation of 5-cyano-2-(3,5-dichlorophenylthio)benzene-1-sulfonyl chloride—4-(3,5-Dichlorophenylthio)-3-aminobenzonitrile (8.000 g, 27.10 mmol) was suspended in 50 mL each of water and concentrated HCl and then chilled in an ice bath. A solution of sodium nitrite (5.610 g, 81.30 mmol) in 50 mL water was added dropwise into the stirring acid suspension. The thus obtained reaction mixture was stirred for an hour while in ice bath. In a separate container, SO$_2$ was bubbled into acetic acid (150 mL) for an hour, to which was then added copper (II) chloride (2.310 g, 13.55 mmol). The copper (II) chloride solution was then stirred for 10 minutes, whereupon the solution turned blue-green, indicating full saturation. The blue-green reaction mixture was chilled in an ice bath. The first reaction mixture (the diazo solution) was added dropwise into the second reaction mixture (saturated acetic acid) while SO$_2$ was still being bubbled through. The SO$_2$ gas source was removed, the thus obtained reaction mixture was stirred for an hour until gas evolution ceased, and then poured solution slowly into vigorously stirred ice water. The resulting suspension was then filtered and the filtered solids rinsed with water to furnish the product as a yellow powder. (6.850 g, 90% purity by $^1$H-NMR, 66.8% yield). $^1$H-NMR: (500 MHz, DMSO-$d_6$) 8.05 (d, J=2 Hz, 1H), 7.72 (t, $J_1$=$J_2$=1 Hz, 1H), 7.64 (dd, $J_1$=8 Hz, $J_2$=2 Hz, 1H), 7.54 (d, J=1 Hz, 2H), 6.97 (d, J=8 Hz, 1H).

4) Preparation of Compound 9—A solution of 5-Cyano-2-(3,5-dichlorophenyl-thio)benzene-1-sulfonyl chloride (1.500 g, 3.96 mmol) in 20 mL CH$_2$Cl$_2$ was added dropwise at a rate of 0.200 mL/min to a stirred solution of 2-piperazinone (0.396 g, 3.96 mmol) and triethylamine (0.823 mL, 5.94 mmol) in 5 mL CH$_2$Cl$_2$. The thus obtained reaction mixture was stirred for 17 hours, whereupon a white precipitate in a brown solution was observed. The solid was filtered and washed with minimal CH$_2$Cl$_2$ to obtain compound 9 as a white powder. (1.071 g, 92.3% purity by HPLC, 61.2% yield). $^1$H-NMR: (500 MHz, DMSO-$d_6$) 8.34 (d, J=2 Hz, 1H), 8.13 (s, 1H), 7.93 (dd, $J_1$=8 Hz, $J_2$=2 Hz, 1H), 7.84 (t, $J_1$=$J_2$=2 Hz, 1H), 7.75 (d, J=2 Hz, 2H), 7.14 (d, J=8 Hz, 1H), 3.90 (s, 2H), 3.60 (m, 2H), 3.21 (m, 2H). ESI-MS: 414 (M+1)$^+$.

Example 2

Preparation of Compound 24

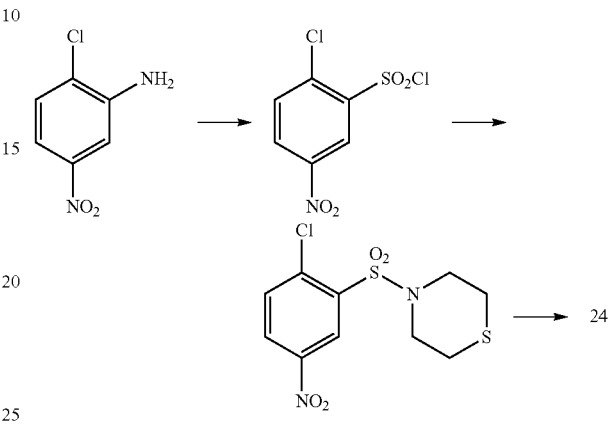

1) Preparation of 2-chloro-5-nitrobenzene-1-sulfonyl chloride—To a solution of 2-chloro-5-nitroaniline (5 g, 28.97 mmol) in 45 mL acetic acid was added 35 mL HCl. The resulting solution was chilled in an ice bath, to which with stirring was added a solution of sodium nitrite (5.997 g, 86.91 mmol) in 15 mL water. The thus obtained reaction mixture was stirred in an ice bath for 1 hour. In a separate container, SO$_2$ was bubbled into acetic acid (40 mL). After 30 minutes, copper (II) chloride (1.435 g, 14.49 mmol) was added and the solution turned dark blue-green, indicating full saturation. The blue-green reaction mixture was chilled in an ice bath. The first reaction mixture (the diazo solution) was added dropwise into the second reaction mixture (saturated acetic acid) while SO$_2$ was still being bubbled through. The SO$_2$ gas source was removed, the thus obtained reaction mixture was stirred for an hour until gas evolution ceased, and then poured solution slowly into vigorously stirred ice water. The resultant solution was then stirred until the ice melted, and filtered to obtain a pink powder. The powder was washed with copious water, furnishing the product as a light pink powder. (4.902 g, 87.3% purity by HPLC, 66.2% yield). 1H-NMR: (500 MHz, DMSO-$d_6$) 8.61 (d, J=3 Hz, 1H), 8.16 (dd, $J_1$=9 Hz, $J_2$=3 Hz, 1H), 7.70 (d, J=9 Hz, 1H).

2) Preparation of 4-(2-chloro-5-nitrophenylsulfonyl)thiomorpholine—To a solution of 2-chloro-5-nitrobenzene-1-sulfonyl chloride (0.200 g, 0.78 mmol) in 8 mL CH$_2$Cl$_2$ was added thiomorpholine (0.111 mL, 1.17 mmol) and triethylamine (0.162 mL, 1.17 mmol). The thus obtained reaction mixture was stirred at room temperature for 18 hours, and was purified via column chromatography (8%→15%→20% EtOAc in Hexanes). Fractions containing the desired product were combined and condensed in vacuo, then triturated with EtOAc and Hexanes. The solids were filtered to obtain the product as a light yellow powder. (0.139 g, 99.6% purity by HPLC, 55.2% yield). $^1$H-NMR: (500 MHz, DMSO-$d_6$) 8.62 (d, J=3 Hz, 1H), 8.47 (dd, $J_1$=9 Hz, $J_2$=3 Hz, 1H), 8.01 (d, J=9 Hz, 1H), 3.54 (m, 4H), 2.65 (m, 4H).

3) Preparation of Compound 24—A solution of 3,5-dichlorothiophenol (0.047 g, 0.26 mmol) in 8 mL THF was chilled in an ice bad. To this solution was added NaH (0.011 g, 0.44 mmol). The solution was then stirred for 5 minutes, after which was added 4-(2-chloro-5-nitrophenylsulfonyl)thiomorpholine (0.0700 g, 0.22 mmol). The thus obtained reaction mixture was stirred for 10 minutes, warmed to room temperature, and then stirred for an additional 18 hours. The reaction mixture was condensed in vacuo and triturated with EtOAc and Hexanes. The solids were filtered to obtain the product as a white powder. (0.096 g, 97.1% purity by HPLC, 93.7% yield). $^1$H-NMR: (500 MHz, DMSO-$d_6$) 8.52 (d, J=1 Hz, 1H), 8.29 (dd, $J_1$=7 Hz, $J_2$=1 Hz, 1H), 7.88 (t, $J_1$=$J_2$=1 Hz, 1H), 7.78 (d, J=1 Hz, 2H), 7.23 (d, J=9 Hz, 1H), 3.59 (m, 4H), 2.70 (m, 4H).

Example 3

Physical Characterization Data

The below compounds were prepared by procedures analogous to those set forth above for compounds 9 and 24.

Compound 1—$^1$H-NMR: (500 MHz, DMSO-$d_6$) 8.22 (d, J=1 Hz, 1H), 7.91 (dd, $J_1$=7 Hz, $J_2$=1 Hz, 1H), 7.84 (t, $J_1$=$J_2$=1 Hz, 1H), 7.71 (d, J=1 Hz, 2H), 7.12 (d, J=8 Hz, 1H), 3.26 (m, 4H), 1.56 (m, 4H), 1.49 (m, 2H). ESI-MS: 427 (M+1)$^+$.

Compound 2—$^1$H-NMR: (500 MHz, DMSO-$d_6$) 8.47 (d, J=8 Hz, 1H), 8.40 (dd, $J_1$=7 Hz, $J_2$=1 Hz, 1H), 8.33 (d, J=1 Hz, 1H), 7.83 (t, $J_1$=$J_2$=1 Hz, 1H), 7.75 (d, J=1 Hz, 2H), 3.19 (m, 4H), 1.54 (m, 4H), 1.46 (m, 2H). ESI-MS: 358 (M+1)$^+$.

Compound 3—$^1$H-NMR: (500 MHz, DMSO-$d_6$) 8.71 (d, J=8 Hz, 1H), 8.48 (dd, $J_1$=7 Hz, $J_2$=1 Hz, 1H), 8.42 (d, J=1 Hz, 1H), 8.03 (t, $J_1$=$J_2$=1 Hz, 1H), 7.90 (d, J=1 Hz, 1H), 3.27 (m, 4H), 1.50 (m, 6H). ESI-MS: 459 (M+1)$^+$.

Compound 4—$^1$H-NMR: (500 MHz, DMSO-$d_6$) 8.18 (d, J=1 Hz, 1H), 7.85 (dd, $J_1$=7 Hz, $J_2$=1 Hz, 1H), 7.23 (s, 3H), 6.92 (d, J=8 Hz, 1H), 3.26 (m, 4H), 2.32 (s, 6H), 1.56 (m, 4H), 1.50 (m, 2H). ESI-MS: 343 (M+1)$^+$.

Compound 5—$^1$H-NMR: (500 MHz, DMSO-$d_6$) 8.19 (d, J=2 Hz, 1H), 7.85 (dd, $J_1$=7 Hz, $J_2$=1 Hz, 1H), 7.22 (s, 3H), 6.93 (d, J=8 Hz, 1H), 3.78 (m, 2H), 2.76 (m, 2H), 2.32 (s, 6H), 1.68 (m, 2H), 1.49 (m, 1H), 1.13 (m, 2H), 0.89 (d, J=7 Hz, 3H). ESI-MS: 441 (M+1)$^+$.

Compound 6—$^1$H-NMR: (500 MHz, DMSO-$d_6$) 8.23 (d, J=1 Hz, 1H), 7.92 (dd, $J_1$=7 Hz, $J_2$=1 Hz, 1H), 7.84 (s, 1H), 7.69 (s, 2H), 7.15 (d, J=8 Hz, 1H), 3.77 (m, 2H), 2.78 (m, 2H), 1.69 (m, 2H), 1.47 (m, 1H), 1.10 (m, 2H), 0.88 (d, J=7 Hz, 3H). ESI-MS: 441 (M+1)$^+$.

Compound 7—$^1$H-NMR: (500 MHz, DMSO-$d_6$) 8.27 (d, J=1 Hz, 1H), 7.92 (dd, $J_1$=7 Hz, $J_2$=1 Hz, 1H), 7.85 (t, $J_1$=$J_2$=1 Hz, 1H), 7.73 (d, J=1 Hz, 2H), 7.13 (d, J=8 Hz, 1H), 4.87 (m, 0.5H), 4.78 (m, 0.5H), 3.40 (m, 4H), 1.94 (m, 2H), 1.79 (m, 2H). ESI-MS: 335 (M+1)$^+$.

Compound 8—$^1$H-NMR: (500 MHz, DMSO-$d_6$) 8 8.26 (d, J=1 Hz, 1H), 7.91 (dd, $J_1$=5 Hz, $J_2$=1 Hz, 1H), 7.84 (t, $J_1$=$J_2$=1 Hz, 1H), 7.68 (d, J=1 Hz, 2H), 7.14 (d, J=8 Hz, 1H), 3.74 (m, 2H), 2.32 (t, $J_1$=$J_2$=12 Hz, 2H), 1.70 (m, 1H), 1.61 (m, 2H), 0.84 (d, J=7 Hz, 6H), 0.68 (m, 1H). ESI-MS: 455 (M+1)$^+$.

Compound 10—$^1$H-NMR: (500 MHz, DMSO-$d_6$) 8.29 (d, J=1 Hz, 1H), 8.14 (s, 1H), 7.88 (dd, $J_1$=7 Hz, $J_2$=1 Hz, 1H), 7.24 (s, 2H), 7.22 (s, 1H), 6.93 (d, J=8 Hz, 1H), 3.90 (s, 2H), 3.59 (m, 2H), 3.20 (m, 2H), 2.32 (s, 6H). ESI-MS: 443 (M+1)$^+$.

Compound 11—$^1$H-NMR: (500 MHz, DMSO-$d_6$) 8.33 (d, J=1 Hz, 1H), 8.13 (dd, $J_1$=7 Hz, $J_2$=1 Hz, 1H), 8.11 (s, 1H), 7.57 (t, $J_1$=$J_2$=1 Hz, 1H), 7.40 (d, J=1 Hz, 2H), 7.30 (d, J=9 Hz, 1H), 3.81 (s, 2H), 3.52 (m, 2H), 3.11 (m, 2H). ESI-MS: 467 (M+1)$^+$.

Compound 12—$^1$H-NMR: (500 MHz, DMSO-$d_6$) 8.23 (s, 1H), 7.94 (d, J=10 Hz, 1H), 7.85 (s, 1H), 7.77 (s, 2H), 7.14 (d, J=8 Hz, 1H), 3.66 (m, 4H), 3.27 (m, 4H). ESI-MS: 369 (M+1)$^+$.

Compound 13—$^1$H-NMR: (500 MHz, DMSO-$d_6$) 8.26 (d, J=1 Hz, 1H), 7.92 (dd, $J_1$=7 Hz, $J_2$=1 Hz, 1H), 7.85 (t, $J_1$=$J_2$=1 Hz, 1H), 7.75 (d, J=1 Hz, 2H), 7.14 (d, J=8 Hz, 1H), 3.58 (m, 4H), 2.68 (m, 4H).

Compound 14—$^1$H-NMR: (500 MHz, DMSO-$d_6$) 8.34 (d, J=1 Hz, 1H), 7.94 (dd, $J_1$=7 Hz, $J_2$=1 Hz, 1H), 7.85 (t, $J_1$=$J_2$=1 Hz, 1H), 7.79 (d, J=1 Hz, 2H), 7.16 (d, J=8 Hz, 1H), 3.84 (m, 4H), 3.29 (m, 4H). ESI-MS: 475 (M−1)$^-$.

Compound 15—$^1$H-NMR: (500 MHz, DMSO-$d_6$) 8.19 (s, 1H), 7.88 (d, J=10 Hz, 1H), 7.26 (s, 2H), 7.23 (s, 1H), 6.94 (d, J=8 Hz, 1H), 3.66 (m, 4H), 3.26 (m, 4H), 2.33 (m, 6H). ESI-MS: 343 (M+1)$^+$.

Compound 16—$^1$H-NMR: (500 MHz, DMSO-$d_6$) 8.22 (d, J=1 Hz, 1H), 7.87 (dd, $J_1$=7 Hz, $J_2$=1 Hz, 1H), 7.24 (s, 2H), 7.22 (s, 1H), 6.94 (d, J=8 Hz, 1H), 3.58 (m, 4H), 2.69 (m, 4H), 2.32 (s, 6H). ESI-MS: 343 (M+1)$^+$.

Compound 17—$^1$H-NMR: (500 MHz, DMSO-$d_6$) 8.30 (d, J=1 Hz, 1H), 7.89 (dd, $J_1$=7 Hz, $J_2$=1 Hz, 1H), 7.26 (s, 2H), 7.23 (s, 1H), 6.96 (d, J=8 Hz, 1H), 3.83 (m, 4H), 3.30 (m, 4H), 2.32 (s, 6H). ESI-MS: 500 (M+1)$^+$.

Compound 18—$^1$H-NMR: (500 MHz, DMSO-$d_6$) 8.36 (s, 2H), 8.31 (s, 1H), 8.26 (d, J=1 Hz, 1H), 7.92 (dd, $J_1$=7 Hz, $J_2$=1 Hz, 1H), 7.14 (d, J=8 Hz, 1H), 3.66 (m, 4H), 3.29 (m, 4H).

Compound 19—$^1$H-NMR: (500 MHz, DMSO-$d_6$) 8.33 (s, 2H), 8.30 (m, 2H), 7.91 (dd, $J_1$=7 Hz, $J_2$=1 Hz, 1H), 7.16 (d, J=8 Hz, 1H), 3.60 (m, 4H), 2.70 (m, 4H).

Compound 20—$^1$H-NMR: (500 MHz, DMSO-$d_6$) 8.37 (m, 3H), 8.31 (s, 1H), 7.93 (dd, $J_1$=7 Hz, $J_2$=1 Hz, 1H), 7.17 (d, J=8 Hz, 1H), 3.86 (m, 4H), 3.30 (m, 4H).

Compound 21—$^1$H-NMR: (500 MHz, DMSO-$d_6$) 8.28 (d, J=1 Hz, 1H), 8.12 (dd, $J_1$=7 Hz, $J_2$=1 Hz, 1H), 7.56 (t, $J_1$=$J_2$=1 Hz, 1H), 7.38 (d, J=1 Hz, 1H), 7.32 (d, J=9 Hz, 1H), 3.48 (m, 4H), 2.65 (m, 4H).

Compound 22—$^1$H-NMR: (500 MHz, DMSO-$d_6$) 8.24 (d, J=1 Hz, 1H), 8.03 (dd, $J_1$=7 Hz, $J_2$=1 Hz, 1H), 6.99 (m, 2H), 6.84 (s, 2H), 3.50 (m, 4H), 2.65 (m, 4H), 2.30 (s, 6H). ESI-MS: 327 (M+1)$^+$.

Compound 23—$^1$H-NMR: (500 MHz, DMSO-$d_6$) 8.33 (d, J=1 Hz, 1H), 8.14 (dd, $J_1$=7 Hz, $J_2$=1 Hz, 1H), 7.57 (t, $J_1$=$J_2$=1 Hz, 1H), 7.42 (d, J=1 Hz, 2H), 7.33 (d, J=9 Hz, 1H), 3.73 (m, 4H), 3.26 (m, 4H). ESI-MS: 526 (M+1)$^+$.

Compound 25—$^1$H-NMR: (500 MHz, DMSO-$d_6$) 8.52 (d, J=1 Hz, 1H), 8.27 (dd, $J_1$=7 Hz, $J_2$=1 Hz, 1H), 7.27 (s, 2H), 7.24 (s, 1H), 7.04 (d, J=9 Hz, 1H), 3.59 (m, 4H), 2.70 (m, 4H), 2.33 (s, 6H). ESI-MS: 363 (M+1)$^+$.

Compound 26—$^1$H-NMR: (500 MHz, DMSO-$d_6$) 8.29 (d, J=1 Hz, 1H), 8.05 (dd, $J_1$=7 Hz, $J_2$=1 Hz, 1H), 7.02 (d, J=9 Hz, 1H), 6.98 (s, 1H), 6.85 (s, 2H), 3.74 (m, 4H), 3.26 (m, 4H), 2.30 (s, 6H). ESI-MS: 484 (M+1)$^+$.

Compound 27—$^1$H-NMR: (500 MHz, DMSO-$d_6$) 8.23 (d, J=1 Hz, 1H), 7.92 (dd, $J_1$=7 Hz, $J_2$=1 Hz, 1H), 7.85 (t, $J_1$=$J_2$=1 Hz, 1H), 7.70 (d, J=1 Hz, 2H), 7.14 (d, J=8 Hz, 1H), 3.59 (m, 2H), 2.91 (m, 1H), 2.67 (m, 3H), 2.32 (m, 1H), 2.26 (m, 1H), 0.95 (d, J=6 Hz, 3H). ESI-MS: 442 (M+1)$^+$.

Compound 30—$^1$H-NMR: (500 MHz, DMSO-$d_6$) 8.57 (d, J=1 Hz, 1H), 8.31 (dd, $J_1$=7 Hz, $J_2$=1 Hz, 1H), 7.89 (t, $J_1$=$J_2$=1 Hz, 1H), 7.83 (d, J=1 Hz, 1H), 7.24 (d, J=9 Hz, 1H), 3.86 (m, 4H), 3.30 (m, 4H). ESI-MS: 495 (M−1)$^-$.

Compound 31—$^1$H-NMR: (500 MHz, DMSO-$d_6$) 8.22 (s, 1H), 7.92 (dd, $J_1$=8 Hz, $J_2$=1 Hz, 1H), 7.83 (s, 1H), 7.72 (s, 1H), 7.13 (d, J=8 Hz, 1H), 3.25 (s, 3H), 3.16 (m, 2H), 2.92 (s, 1H), 2.73 (m, 2H), 1.23 (m, 2H). ESI-MS: 469 (M+1)$^+$.

Compound 32—$^1$H-NMR: (500 MHz, DMSO-d$_6$) 8.26 (d, J=1Hz, 1H), 7.93 (dd, J$_1$=7 Hz, J$_2$=1 Hz, 1H), 7.86 (t, J$_1$=J$_2$=1 Hz, 1H), 7.73 (d, J=1 Hz, 2H), 7.13 (d, J=8 Hz, 1H), 3.59 (m, 1H), 3.57 (s, 3H), 3.28 (m, 1H), 3.23 (m, 1H), 3.13 (m, 1H), 2.98 (m, 1H), 2.83 (m, 1H), 2.68 (m, 1H). ESI-MS: 376 (M−1)$^−$.

Example 4

CCR3 Receptor Binding Assay

Cells were washed once with PBS and resuspended in a binding buffer (25 mM HEPES pH 7.6, 5 mM MgCl$_2$, 1 mM CaCl$_2$, 0.5% BSA, 0.1% NaN$_3$). 100 mL of cell suspension (2×10$^5$ cells/well) and 0.1 nM [$^{125}$I]-labeled human eotaxin/CCL11 (2000 Ci/mmol specific activity) were mixed in a 96-well U-bottom polypropylene plate, and incubated for 60 min at room temperature for the binding reaction. The cell suspension was then transferred to a filtration plate (#MAFB, Millipore), and washed 3 times with the binding buffer containing 0.5 M NaCl, scintillant added, and the radioactivity was counted on a TopCount (Packard). For the determination of non-specific binding, the cell suspension and [$^{125}$I]-labeled human eotaxin/CCL11 were incubated in the presence of 500 nM of unlabeled human eotaxin/CCL11. See, lino et al., "Molecular cloning and functional characterization of cynomolgus monkey (*Macaca fascicularis*) CC chemokine receptor, CCR3," *Cytokine* 2002, 19, 276-286.

Biological results are summarized in Table 1, wherein A represents a value no greater than 50 nM, and B represents a value greater than 50 nM but no greater than 500 nM, C represents a value greater than 500 nM but no greater than 5 μM, and D represents a value greater than 5 μM.

TABLE 1

| Cmpd # | K$_i$ |
|---|---|
| 1 | B |
| 2 | D |
| 3 | D |
| 4 | A |
| 5 | D |
| 6 | D |
| 7 | A |
| 8 | D |
| 9 | A |
| 10 | A |
| 11 | A |
| 12 | A |
| 13 | A |
| 14 | A |
| 15 | D |
| 16 | D |
| 17 | A |
| 18 | C |
| 19 | D |
| 20 | D |
| 21 | B |
| 22 | D |
| 23 | A |
| 24 | D |
| 25 | D |
| 26 | D |
| 27 | A |
| 28 | A |
| 29 | A |
| 30 | A |
| 31 | A |
| 32 | A |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula I:

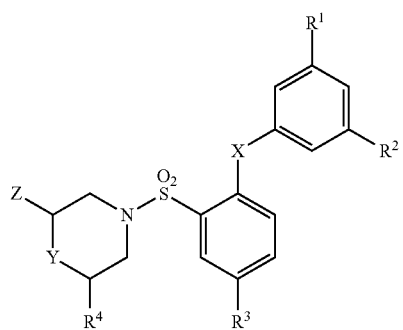

or a pharmaceutically acceptable salt, stereoisomer, or tautomer thereof; wherein:
X is S, SO, or SO$_2$;
Y is S or SO$_2$;
Z is hydrogen or C$_{1-6}$ alkyl optionally substituted by aryl, hydroxy, carboxy, alkoxy, carbamoyl, or halo;
R$^1$ and R$^2$ are each independently halogen, C$_{1-6}$ alkyl, or C$_{1-6}$ haloalkyl;
R$^3$ is CN or NO$_2$; and
R$^4$ is hydrogen or C$_{1-6}$ alkyl optionally substituted by aryl, hydroxy, carboxy, alkoxy, carbamoyl, or halo.

2. The compound of claim 1, wherein X is S.
3. The compound of claim 1, wherein R$^3$ is CN.
4. The compound of claim 1, wherein R$^3$ is NO$_2$.
5. A compound having the structure of Formula II:

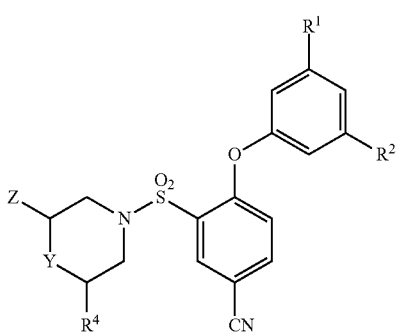

or a pharmaceutically acceptable salt, stereoisomer or tautomer thereof; wherein:
Y is S or SO$_2$;
Z is hydrogen or C$_{1-6}$ alkyl optionally substituted by aryl, hydroxy, carboxy, alkoxy, carbamoyl, or halo;
R$^1$ and R$^2$ are each independently halogen, C$_{1-6}$ alkyl, or C$_{1-6}$ haloalkyl; and $R^4$ is hydrogen or $C_{1-6}$ alkyl optionally substituted by aryl, hydroxy, carboxy, alkoxy, carbamoyl, or halo.

6. The compound of claim 1, wherein Z is H.
7. The compound of claim 1, wherein Z is $CH_3$.
8. The compound of claim 1, wherein Y is S.
9. The compound of claim 1, wherein Y is $SO_2$.
10. The compound of claim 1, wherein $R^1$ and $R^2$ are each Cl.
11. The compound of claim 1, wherein $R^1$ and $R^2$ are each $CH_3$.
12. The compound of claim 1, wherein $R^1$ and $R^2$ are each $CF_3$.
13. The compound of claim 1, wherein $R^4$ is H.
14. A compound selected from the group consisting of:

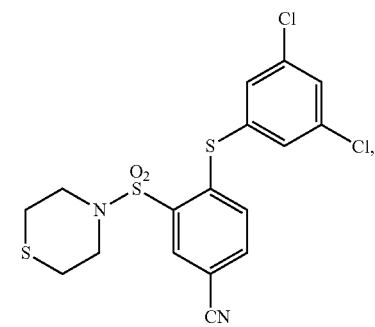

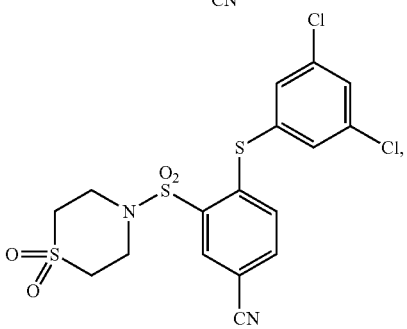

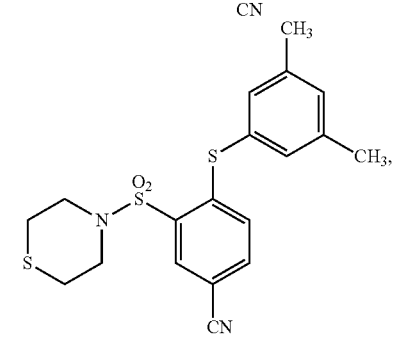

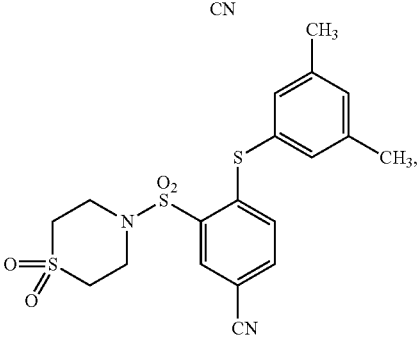

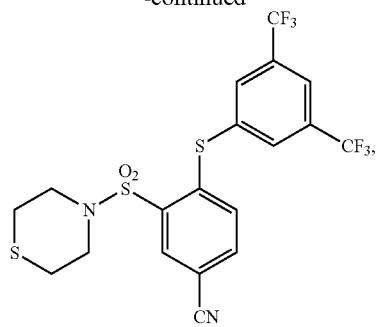

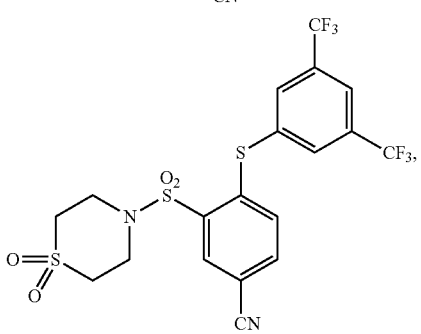

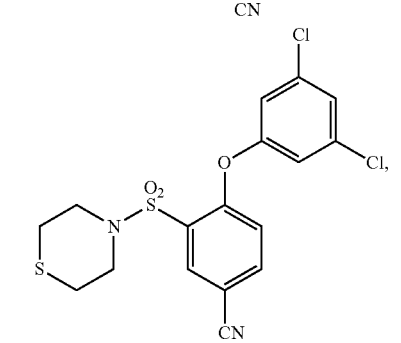

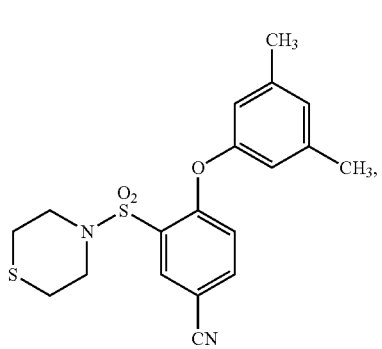

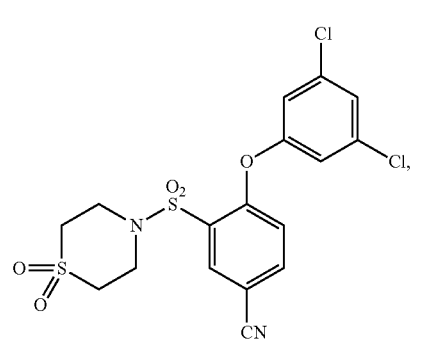

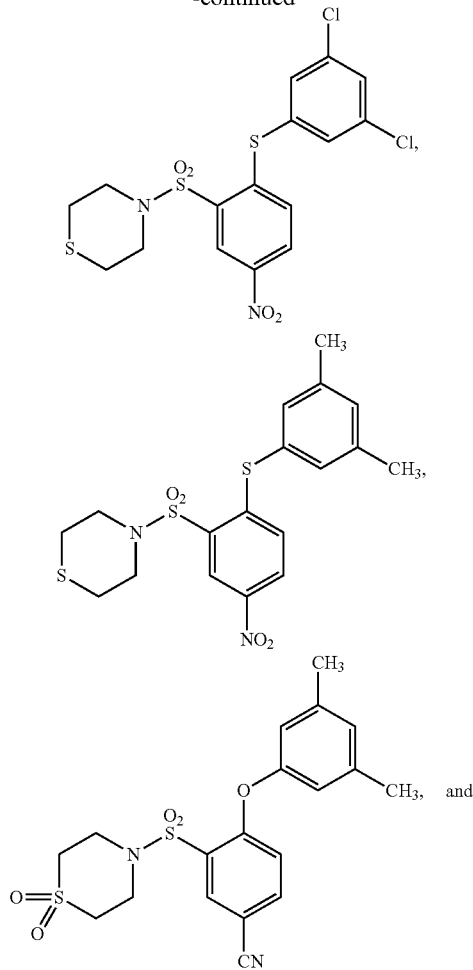

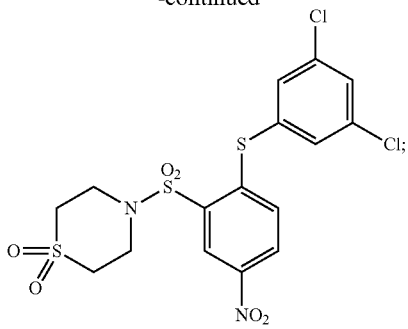

and pharmaceutically acceptable salts, stereoisomers, and tautomers thereof.

15. A pharmaceutical composition comprising the compound of claim 1 and one or more pharmaceutically acceptable carriers or excipients.

16. A method for treating one or more symptoms of a disorder, disease, or condition in a subject, comprising administering to the subject the compound of claim 1; wherein the disorder, disease, or condition is asthma, rhinitis, allergic disease, HIV, or lung granuloma.

17. The method of claim 16, wherein the disorder or disease is asthma, rhinitis, or an allergic disease.

18. The method of claim 16, wherein the disorder or disease is HIV or lung granuloma.

19. The method of claim 16, wherein the compound is administered orally, parenterally, or topically.

20. The method of claim 16, wherein the compound is administered in combination with a second therapeutic agent.

* * * * *